(12) United States Patent
Lane et al.

(10) Patent No.: US 9,554,793 B2
(45) Date of Patent: Jan. 31, 2017

(54) MEANS AND METHODS FOR SUTURING TISSUE

(71) Applicant: SafePath Medical, Inc., Methuen, MA (US)

(72) Inventors: Joseph P. Lane, Amesbury, MA (US); Michael W. Sutherland, Pelham, NH (US); Thomas D. Egan, Marblehead, MA (US); David P. Dolan, Londonderry, NH (US)

(73) Assignee: SAFEPATH MEDICAL, INC., Amesbury, MA (US)

( * ) Notice: Subject to any disclaimer, the term of this patent is extended or adjusted under 35 U.S.C. 154(b) by 0 days.

(21) Appl. No.: 14/216,816

(22) Filed: Mar. 17, 2014

(65) Prior Publication Data

US 2014/0276989 A1    Sep. 18, 2014

Related U.S. Application Data

(60) Provisional application No. 61/802,456, filed on Mar. 16, 2013.

(51) Int. Cl.
*A61B 17/062* (2006.01)
*A61B 17/04* (2006.01)
(Continued)

(52) U.S. Cl.
CPC ....... *A61B 17/0625* (2013.01); *A61B 17/0482* (2013.01); *A61B 2017/00849* (2013.01);
(Continued)

(58) Field of Classification Search
CPC . A61B 17/0483; A61B 17/0469; A61B 17/04; A61B 17/06114; A61B 17/0625; A61B 17/0482; A61B 17/062; A61B 2017/2927; A61B 2017/0608; A61B 2017/2929
(Continued)

(56) References Cited

U.S. PATENT DOCUMENTS 1,676,582 A    7/1928   Stuart
2,336,690 A   12/1943   Karle
(Continued)

OTHER PUBLICATIONS

U.S. Appl. No. 12/833,006, filed Jul. 9, 2011, McClurg et al.

*Primary Examiner* — Eric Rosen
*Assistant Examiner* — George J Ulsh
(74) *Attorney, Agent, or Firm* — Leason Ellis LLP

(57) ABSTRACT

A device according to one exemplary embodiment is a compact, light-weight handheld device that includes a needle and suture assembly, a mechanism for gripping and releasing the needle and suture assembly (a "needle transfer mechanism" or "needle shuttle mechanism"), safely capturing the needle assembly upon exit from the patient's tissue, and returning the needle to position such that the process of delivering additional sutures to the patient can be repeated. The device of the present invention accommodates the right or left-handed user, rests comfortably in the user's hand, allows sufficient visualization of the procedure site, and permits the user to either control penetration depth of the needle or default to a device-determined depth. The present device permits the user to utilize a wrist-rotation (pivoting) suture delivery technique that is familiar to a user based on experience with other surgical techniques.

21 Claims, 31 Drawing Sheets

(51) Int. Cl.
*A61B 17/06* (2006.01)
*A61B 17/00* (2006.01)

(52) U.S. Cl.
CPC .............. *A61B 2017/0608* (2013.01); *A61B 2017/06052* (2013.01)

(58) Field of Classification Search
USPC ................................................ 606/144, 147
See application file for complete search history.

(56) References Cited

U.S. PATENT DOCUMENTS

| | | |
|---|---|---|
| 4,109,428 A | 8/1978 | Aarons |
| 4,373,530 A | 2/1983 | Kilejian |
| 4,406,237 A | 9/1983 | Eguchi et al. |
| 4,414,908 A | 11/1983 | Eguchi et al. |
| 4,608,800 A | 9/1986 | Fredette |
| 4,621,640 A | 11/1986 | Mulhollan et al. |
| 4,957,498 A | 9/1990 | Caspari et al. |
| 4,969,302 A | 11/1990 | Coggan et al. |
| 5,234,443 A | 8/1993 | Phan et al. |
| 5,426,901 A | 6/1995 | Indracek |
| 5,437,681 A | 8/1995 | Meade et al. |
| 5,457,923 A | 10/1995 | Logan et al. |
| 5,499,990 A | 3/1996 | Schülken et al. |
| 5,571,090 A | 11/1996 | Sherts |
| 5,571,119 A | 11/1996 | Atala |
| 5,609,597 A | 3/1997 | Lehrer |
| 5,643,292 A | 7/1997 | Hart |
| 5,665,109 A | 9/1997 | Yoon |
| 5,694,726 A | 12/1997 | Wu |
| 5,709,693 A | 1/1998 | Taylor |
| 5,728,113 A | 3/1998 | Sherts |
| 5,729,933 A | 3/1998 | Strength |
| 5,730,747 A | 3/1998 | Ek et al. |
| 5,746,751 A | 5/1998 | Sherts |
| 5,759,188 A | 6/1998 | Yoon |
| 5,766,186 A | 6/1998 | Faraz et al. |
| 5,824,009 A | 10/1998 | Fukuda et al. |
| 5,843,100 A | 12/1998 | Meade |
| 5,860,992 A | 1/1999 | Daniel et al. |
| 5,871,488 A | 2/1999 | Tovey et al. |
| 5,904,692 A | 5/1999 | Steckel et al. |
| 5,908,428 A | 6/1999 | Scirica et al. |
| 5,919,202 A | 7/1999 | Yoon |
| 5,935,149 A | 8/1999 | Ek |
| 5,951,575 A | 9/1999 | Bolduc et al. |
| 5,954,733 A | 9/1999 | Yoon |
| 5,957,937 A | 9/1999 | Yoon |
| 5,984,932 A | 11/1999 | Yoon |
| 5,993,466 A | 11/1999 | Yoon |
| 5,993,467 A | 11/1999 | Yoon |
| 6,026,616 A | 2/2000 | Gibson |
| 6,048,351 A | 4/2000 | Gordon et al. |
| 6,071,289 A | 6/2000 | Stefanchik et al. |
| 6,099,550 A | 8/2000 | Yoon |
| 6,099,553 A | 8/2000 | Hart et al. |
| 6,159,224 A | 12/2000 | Yoon |
| 6,224,614 B1 | 5/2001 | Yoon |
| 6,277,132 B1 | 8/2001 | Brhel |
| 6,533,795 B1 | 3/2003 | Tran et al. |
| 6,539,675 B1 | 4/2003 | Gile |
| 6,643,990 B2 | 11/2003 | Jensen |
| 6,911,034 B2 | 6/2005 | Nobles et al. |
| 6,923,819 B2 | 8/2005 | Meade et al. |
| 6,984,237 B2 | 1/2006 | Hatch et al. |
| 6,997,932 B2 | 2/2006 | Dreyfuss et al. |
| 7,011,668 B2 | 3/2006 | Sancoff et al. |
| 7,033,370 B2 | 4/2006 | Gordon et al. |
| 7,060,077 B2 | 6/2006 | Gordon et al. |
| 7,090,686 B2 | 8/2006 | Nobles et al. |
| 7,108,700 B2 | 9/2006 | Chan et al. |
| 7,188,454 B2 | 3/2007 | Mowery et al. |
| 7,316,694 B2 | 1/2008 | Reinitz |
| 7,318,282 B2 | 1/2008 | Pulte |
| 7,326,221 B2 | 2/2008 | Sakamoto et al. |
| 7,331,970 B2 | 2/2008 | Almodovar et al. |
| 7,338,504 B2 | 3/2008 | Gibbens et al. |
| 7,442,198 B2 | 10/2008 | Gellman et al. |
| 7,544,199 B2 | 6/2009 | Bain et al. |
| 7,572,265 B2 | 8/2009 | Stone et al. |
| 7,582,096 B2 | 9/2009 | Gellman et al. |
| 7,588,583 B2 | 9/2009 | Hamilton et al. |
| 7,615,059 B2 | 11/2009 | Watschke et al. |
| 7,628,796 B2 | 12/2009 | Shelton et al. |
| 7,704,262 B2 | 4/2010 | Bellafiore et al. |
| 7,746,179 B1 | 7/2010 | Schiedegger et al. |
| 7,793,475 B2 | 9/2010 | Riggs |
| 7,997,043 B1 | 8/2011 | MacMillan et al. |
| 7,998,149 B2 | 8/2011 | Hamilton et al. |
| 8,006,441 B2 | 8/2011 | Pulte |
| 8,172,860 B2 | 5/2012 | Zung et al. |
| 8,252,007 B2 | 8/2012 | Hamilton et al. |
| 8,257,371 B2 | 9/2012 | Hamilton et al. |
| 8,317,805 B2 | 11/2012 | Hamilton et al. |
| 8,419,754 B2 | 4/2013 | Laby et al. |
| 8,603,113 B2 | 12/2013 | Hamilton et al. |
| 8,617,187 B2 | 12/2013 | Hamilton et al. |
| 8,685,045 B2 | 4/2014 | Hamilton et al. |
| 8,758,391 B2 * | 6/2014 | Swayze .............. A61B 17/0682 606/205 |
| 2002/0087178 A1 | 7/2002 | Nobles et al. |
| 2002/0088189 A1 | 7/2002 | Honda |
| 2002/0124485 A1 | 9/2002 | Pulte |
| 2003/0023250 A1 | 1/2003 | Watschke |
| 2003/0181926 A1 * | 9/2003 | Dana ................... A61B 17/0485 606/148 |
| 2004/0243147 A1 | 12/2004 | Lipow |
| 2005/0043747 A1 | 2/2005 | Field et al. |
| 2005/0085857 A1 | 4/2005 | Peterson et al. |
| 2005/0119670 A1 | 6/2005 | Kerr |
| 2005/0234479 A1 | 10/2005 | Hatch et al. |
| 2005/0267529 A1 | 12/2005 | Crockett et al. |
| 2006/0069396 A1 | 3/2006 | Meade et al. |
| 2006/0075712 A1 | 4/2006 | Gilbert et al. |
| 2006/0196144 A1 | 9/2006 | Spek |
| 2006/0282088 A1 | 12/2006 | Ryan |
| 2007/0021755 A1 | 1/2007 | Almodovar |
| 2007/0060930 A1 | 3/2007 | Hamilton et al. |
| 2007/0060931 A1 | 3/2007 | Hamilton et al. |
| 2007/0062140 A1 | 3/2007 | Sillik |
| 2007/0088372 A1 | 4/2007 | Gellman et al. |
| 2007/0225735 A1 | 9/2007 | Stone et al. |
| 2007/0270885 A1 | 11/2007 | Weinert et al. |
| 2008/0243147 A1 | 10/2008 | Hamilton et al. |
| 2008/0249545 A1 | 10/2008 | Shikhman |
| 2009/0012538 A1 | 1/2009 | Saliman et al. |
| 2009/0024145 A1 | 1/2009 | Meade et al. |
| 2009/0157105 A1 | 6/2009 | Zung et al. |
| 2009/0292300 A1 | 11/2009 | Hamilton et al. |
| 2010/0010512 A1 | 1/2010 | Taylor et al. |
| 2010/0016608 A1 | 1/2010 | Kim |
| 2010/0030238 A1 | 2/2010 | Viola et al. |
| 2010/0063519 A1 * | 3/2010 | Park ................... A61B 17/0491 606/144 |
| 2010/0152751 A1 | 6/2010 | Meade et al. |
| 2010/0268257 A1 | 10/2010 | Hamilton et al. |
| 2010/0280530 A1 | 11/2010 | Hashiba |
| 2011/0251627 A1 | 10/2011 | Hamilton et al. |
| 2011/0313433 A1 | 12/2011 | Woodard, Jr. et al. |
| 2012/0165837 A1 | 6/2012 | Belman et al. |
| 2012/0316580 A1 | 12/2012 | Belman et al. |
| 2013/0041388 A1 | 2/2013 | Lane et al. |
| 2013/0165954 A1 | 6/2013 | Dreyfuss et al. |
| 2013/0231687 A1 | 9/2013 | Laby et al. |
| 2013/0245646 A1 | 9/2013 | Lane et al. |
| 2013/0304096 A1 | 11/2013 | Nguyen et al. |
| 2014/0222036 A1 | 8/2014 | Hamilton et al. |
| 2014/0276988 A1 | 9/2014 | Tagge et al. |
| 2014/0288581 A1 | 9/2014 | Hamilton et al. |

* cited by examiner

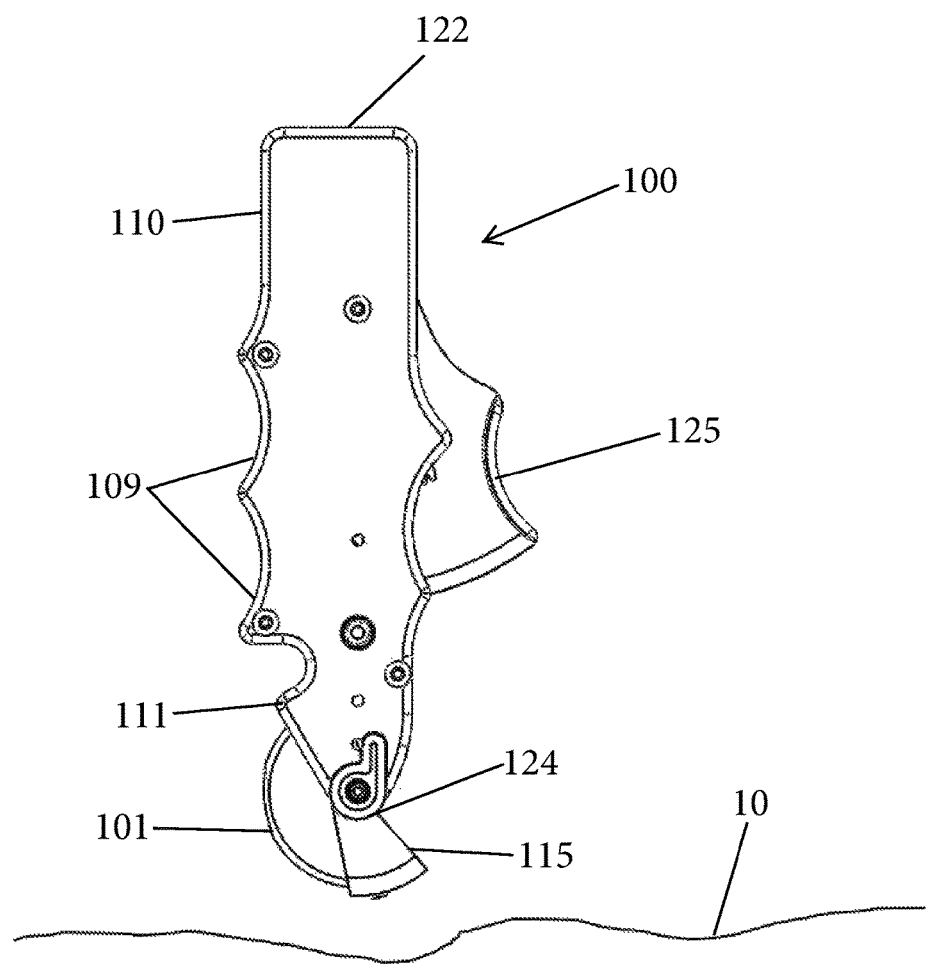

FIG. 3 (windup mechanism)
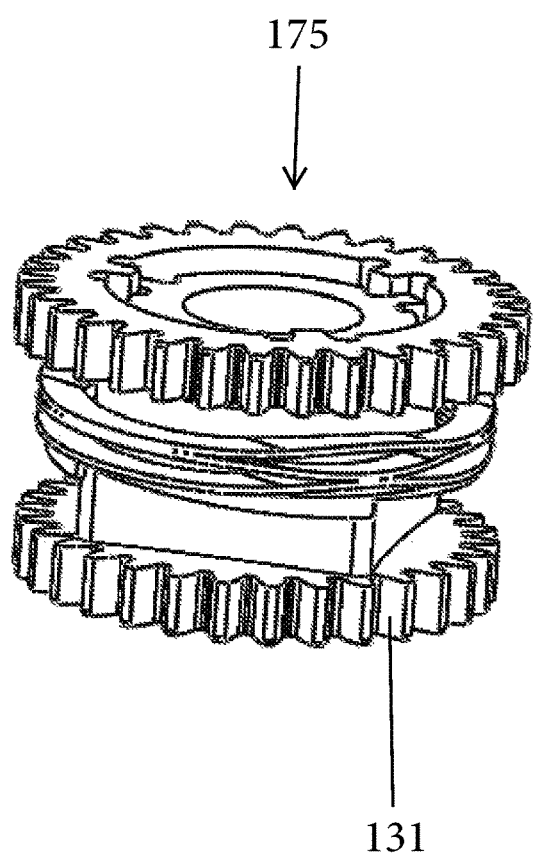

FIG. 4 (lever clamp force multiplier)
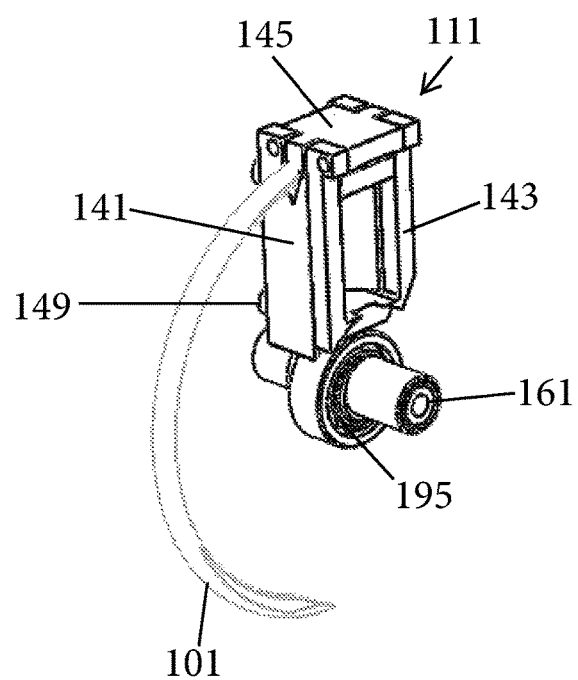

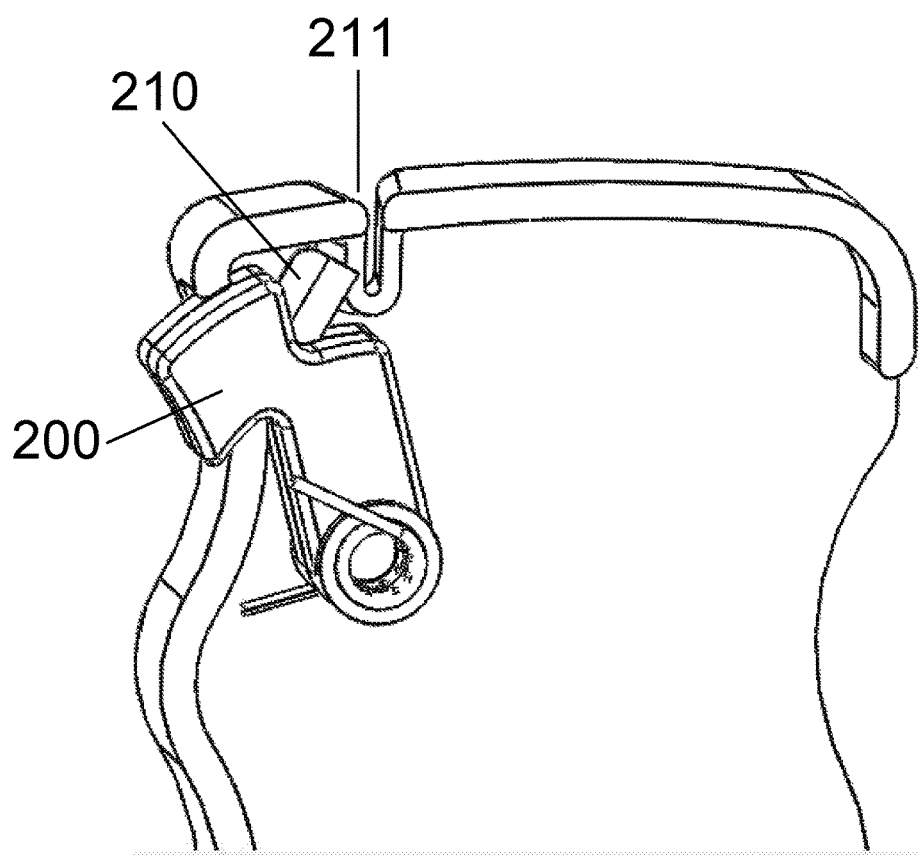
FIG. 10 (cutter)

FIG. 11 (cutter)
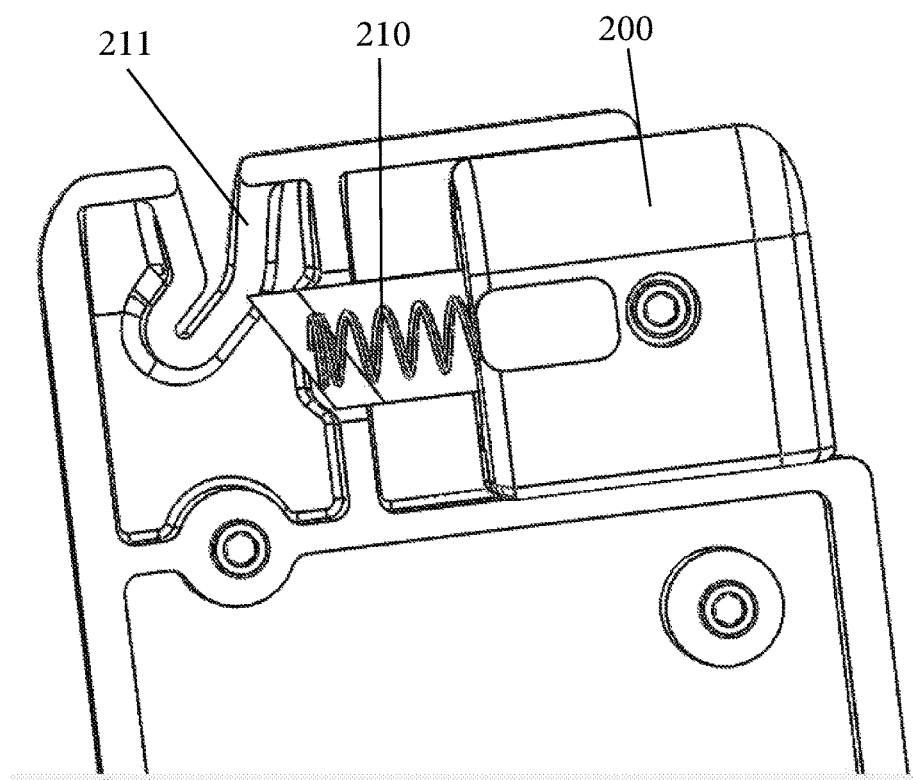

FIG. 12 (safety shields)
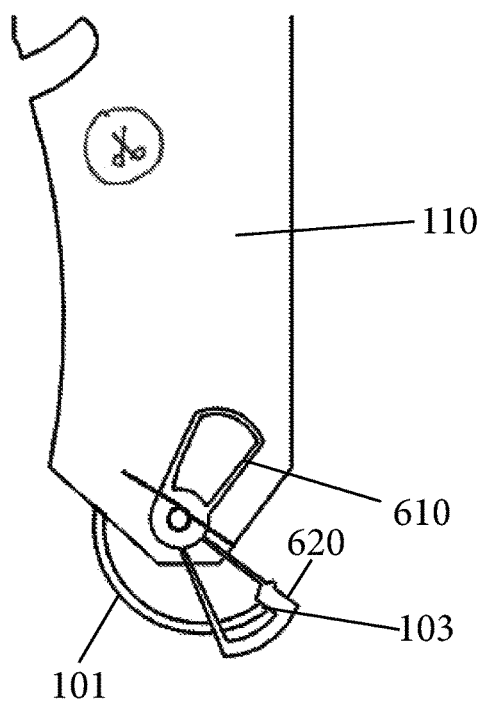

MEANS AND METHODS FOR SUTURING TISSUE

CROSS-REFERENCE TO RELATED APPLICATION

The present application claims the benefit of U.S. patent application Ser. No. 61/802,456, filed Mar. 16, 2013, which is hereby incorporated by reference in its entirety.

BACKGROUND

Needles and suture are used throughout the healthcare industry for indications such as wound and incision closure, securing catheters, and affixing implantable meshes, annuloplasty rings, and other medical apparatus. These sutures are used on the surface of the patient's skin as well as through laparoscopic, endoscopic, and surgical procedures. Because needles represent injury and illness risks to the user, there is a need to make needle usage safer without sacrificing ease of use, performance, and cost. A medical device that can be used to safely suture the tissue of a patient will be valuable to physicians, surgeons, nurses, physician assistants, military personnel, and other clinical and non-clinical users of suture.

SUMMARY

A device according to one exemplary embodiment is a compact, light-weight handheld device that includes a needle and suture assembly, a mechanism for gripping and releasing the needle and suture assembly (a "needle transfer mechanism" or "needle shuttle mechanism"), safely capturing the needle assembly upon exit from the patient's tissue, and returning the needle to a position such that the process of delivering additional sutures to the patient can be repeated. The device of the present invention accommodates the right or left-handed user, rests comfortably in the user's hand, allows sufficient visualization of the procedure site, and permits the user to either control penetration depth of the needle or default to a device-determined depth. The present device permits the user to utilize a wrist-rotation (pivoting) suture delivery technique that is familiar to a user based on experience with other surgical techniques.

BRIEF DESCRIPTION OF THE DRAWING FIGURES

FIG. 1a is a side elevation view of a suture device according to a first embodiment in a first position;

FIG. 3 is a perspective view of a windup mechanism;

FIG. 4 is a lever clamp force multiplier;

FIG. 10 is a perspective view of a suture cutter;

FIG. 11 is a perspective view of another suture cutter;

FIG. 12 is side view of safety shields;

DETAILED DESCRIPTION OF CERTAIN EMBODIMENTS

Figure 1B:
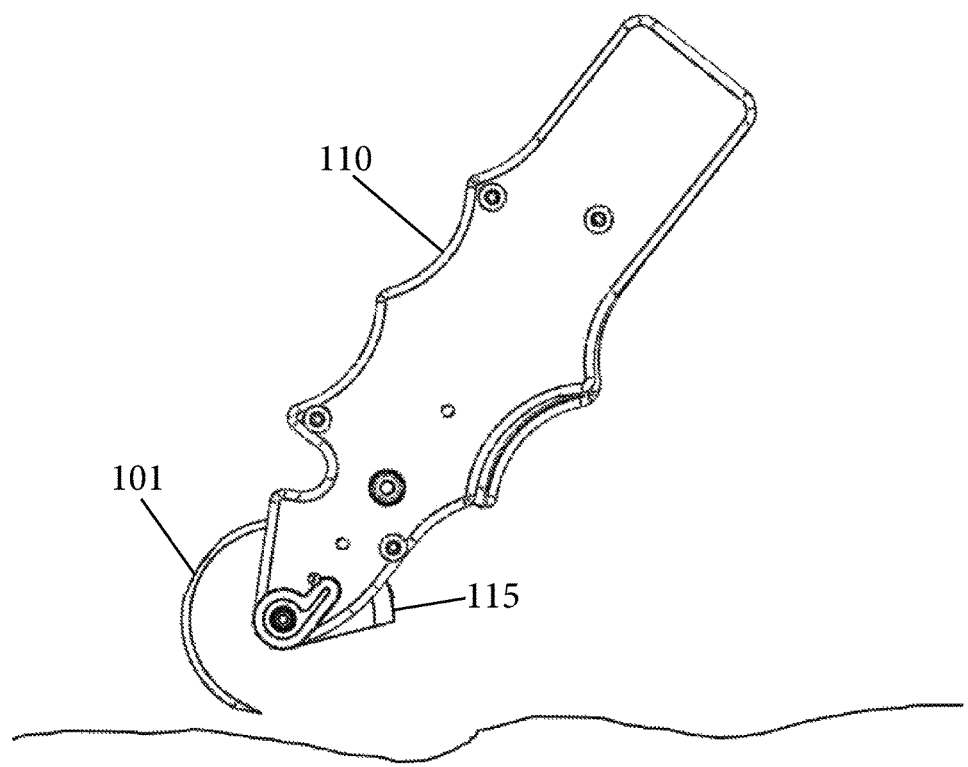
FIG. 1b is a side elevation view of the suture device in a second position.

Disclosed herein are device concepts and methods for safely suturing tissue, skin, muscle, ligament, tendon and similar structures throughout the entire body. Healthcare workers need a safe method and device for closing wounds and incisions, approximating tissue, securing meshes and annuloplasty rings, securing catheters to a patient, and related functions. The current procedure typically consists of a user grasping an unprotected needle and suture with hemostats, a needle driver, forceps, or suturing device and then piercing the patient's tissue by utilizing hand, wrist, and device movements. In this scenario, the needle point is exposed to the user before, during, and after the procedure and provides risk for accidental needle stick injuries (NSI) to the user and procedural staff. These NSIs can transmit bloodborne pathogens such as hepatitis and HIV to the user and others from the patient and potentially cause illness or death. Users that are injured in this manner are required to report the injury, undergo diagnostic tests and begin receiving prophylactic treatment. They may also be required to take a leave of absence from work or continue indefinitely with a prescribed drug regimen.

A device according to one exemplary embodiment is a compact, light-weight handheld device that includes a needle and suture assembly, a mechanism for gripping and releasing the needle and suture assembly (a "needle transfer mechanism" or "needle shuttle mechanism"), safely capturing the needle assembly upon exit from the patient's tissue, and returning the needle to a position such that the process of delivering additional sutures to the patient can be repeated. The device of the present invention accommodates the right or left-handed user, rests comfortably in the user's hand, allows sufficient visualization of the procedure site, and permits the user to either control penetration depth of the needle or default to a device-determined depth. The present device permits the user to utilize a wrist-rotation (pivoting) suture delivery technique that is familiar to a user based on experience with other surgical techniques.

In a preferred embodiment, the device has the following definitive advantages over current art: Safety: The user cannot contact the point of the needle and is able to avoid accidental NSIs and the human and financial costs associated with those accidents. Performance: The device allows the user to reproduce the needle delivery motion that is currently used by healthcare workers. This improves the accuracy and integrity of the securement and reduces the trauma to the patient. Size: The device is sized and oriented for easy access to crowded and narrow regions of the patient's body such as the neck; Ease of Use: The device can be generally operated with one hand, by right-handed and left handed users, and multiple sutures are able to be secured to the patient through a minimal series of steps. Cost: The device is designed as a single use device that is economical and easy to manufacture. Versatility: The device is suitable for use within a hospital environment and any first aid setting. It can be utilized to secure nearly every type of catheter and to close wounds. In addition, it may be packaged within catheter and medical accessory sets or as a stand-alone device.

In one exemplary embodiment, the needle within this device can be returned to its starting point after it crosses the patient's tissue so that the device can be used to repeat the needle delivery process multiple times. At the conclusion of the process, the needle is safely retained by a mechanism within the device, which can then be safely disposed. In this embodiment, safety features are incorporated into the device such that the user cannot come into contact with the needle before, during, and after the procedure. In addition, an integral cutter is incorporated into the device in order that the suture can be cut by the user without the need for scissors or a scalpel. At the conclusion of each suture delivery, the safety features are automatically engaged and needle is safely shielded from the user. Additional elements within this embodiment include an integral cutter in order that the suture can be cut or trimmed by the user without the need for a separate scissors or scalpel.

Although it is contemplated as a single-use device, it is understood that slight alterations can be made to the design and materials that would allow said device to be resterilized, reloaded with an additional needle and suture, and reused. It may be further contemplated that the distally mounted needle has the ability to rotate relative to the handle and replicate the manual needle-driving motion of crossing tissue that is currently used in and outside the clinic. This is particularly useful in laparoscopic, endoscopic, and surgical procedures when the user's natural range of motion is compromised.

Looking again at the primary embodiment, the handle, which is comprised of one or more components such as a housing, actuator, and buttons, may be molded, cast or extruded from a variety of materials including but not limited to polymers or metals. Examples of polymers suitable for fabricating the handle are thermoplastic and thermosetting materials such as polystyrene, acrylic, polycarbonate, polyamide, polyester, polyetherimide, polysulfone, polylactic acid, polyvinylchloride, polyolefins, polyurethane, fluoropolymers, and copolymers and alloys thereof. These materials may be filled with glass or other useful reinforcing agents in order to enhance their mechanical properties. Suitable metals come from but are not limited to a group including titanium alloys and stainless steel. The selected materials must meet physical and mechanical performance requirements and be able to withstand sterilization methods employed within the medical device industry such as ethylene oxide or gamma irradiation. The handle design may be constructed to be linear and longitudinal, non-planar, angled, arcuate or a combination of these conformations.

The needle assembly generally consists of a suturing needle and a suture attached thereto. The suturing needle includes a distal pointed end suitable for piercing and crossing tissue and a blunt proximal end suitable for affixing a suture, and a body between the distal and proximal ends. The suturing needle can be fabricated in a variety of configurations from straight to curved and be monolithic or of a multi-part construction. The outer diameters of the needles can be round or non-round, tapered, or possesses features that assist in advancing and gripping the needle, i.e., flats. Longitudinal ribs or recessions or other features found on the outer diameter of the needle may provide additional rigidity and enhance the needle's ability to effectively cross tissue. Needles are commonly made from stainless steel and related alloys but can be made from other metals, polymers and ceramic materials that are sufficiently rigid, capable of possessing and sustaining a functionally sharp distal point, and able to bond to suture. Traditionally, sutures are affixed to the proximal end of metal needles by swaging, crimping, and adhesives. Suture attachment can also be configured such that the suture is affixed to the other regions of the needle, yet not the proximal terminus. This design variant provides additional freedom for suture management and gripping the needle in the device handle. Coatings on the needle serve to enhance the lubricity of the needle and reduce tissue penetration forces.

The suture is the thread-like material that is used to treat internal and external wounds and incisions and to secure catheters or other components to patients. It comes in a variety of diameters, textures, forms, i.e., single strand or braided, and materials depending upon the desired properties and intended application. Sutures can be absorbable, i.e., collagen, polyglactin, polydioxanone, polyglycolide-lactide copolymers, or non-absorbable, i.e., silk, nylon, polyester, polypropylene, stainless steel. They can be treated with antimicrobial, bioabsorbable, hydrophilic or other functional additives. In addition, they can have surface features that permit the suture to be drawn smoothly through tissue in one direction but snag the tissue when pulled in the opposite direction. This is advantageous when the user wants to temporarily or permanently approximate tissue without the need to tie a knot.

The interfaces between the handle and the suturing needle/suture are generally referred to as the mechanisms or assemblies. These mechanisms serve to grasp, release, and shuttle the needle by manipulations to the handle by the user or by otherwise manipulating the device to cause the needle transfer. As will be appreciated from the below detailed description, there are a number of mechanical mechanisms that can be used to produce the desired movement of the suturing needle and more specifically, produce a reciprocal needle transfer action in which the suturing needle is initially held in one position within the mechanism and is then caused to be moved to another position within the mechanism to effectuate the suture needle passing into and through the tissue and then being subsequently extracted from the tissue. Further, after extraction, the mechanism is preferably designed to pass the suturing needle back from the needle capture/extraction position to the initial position at which the process can be repeated. Thus, one mechanism can be thought of as being a mechanism for cycling the suturing needle between different positions that result in the desired suturing action.

It will thus be appreciated that a variety of mechanisms that are able to grasp, release, and shuttle the needle can be used. The mechanisms include but are not limited to rack and pinion, gearing, cams, ramps, screw bodies, springs, multiple-point gripping structures, i.e., 3-point, collets, drive belts, and rigid and flexible push rods to name a few. In instances, the suturing needle can comprise physical features that correspond to engagement features found within these mechanisms in order, for example, to increase grip strength. Some examples of these features are indentations, serrations, projections, faces, flats, undercuts, rings, and ports.

Moreover, the present device preferably includes a safety shield mechanism, which protects the user from the needle point before, during, and after the suturing procedure. The safety shield mechanism can exist in numerous forms in that any number of different mechanical arrangements can be used to accomplish the intended function. The safety shield mechanism can comprise single or multiple components, be biased to a safety-mode position and/or be user actuated, and/or have reversible or irreversible lock-out features. The safety shield mechanism can be configured, for example, as a slideable or rotatable cover, or as deflectable wing-like shields that obstruct user access to the needle point. Similar to the handle described above, the safety shield mechanism cans be made from a wide range of thermoplastics and thermosetting polymers; however, a transparent polymer may be more desired as it would provide the user with greater visibility of the needle and suturing site. Furthermore, the safety shield mechanism can be manufactured from metals, such as stainless steel, titanium, and titanium alloys including nickel-titanium, and configured as a wireform, mesh, grid, or strut. A spring or other force-resilient components can be incorporated in order to bias the safety apparatus into a safe position or to actuate multiple components that comprise the safety apparatus.

Referring to the lockout feature above, it will prevent the user from accidentally exposing the needle and obtaining an NSI. The lockout generally takes the form of a user-actuated button, lever, slide, or other similar means and a connecting element that couples the actuation means and the safety apparatus. The button causes the connecting element to lock and unlock the apparatus in a variety of ways. Examples of these means include tongue and groove, intermeshing gears, friction and interference fits, inclined planes, cantilever, and screws. In each of these methods, the connecting element restricts the movement of the apparatus, and therefore, the exposure of the needle until the user actuates the button to release the apparatus.

Finally, a suture cutter is preferably located within the device handle so that the user can trim knotted sutures and suture strands to length. One exemplary cutter can be a dynamic shearing apparatus, i.e., scissors or slideable blade(s), that requires the user to press or slide a button or manipulate an actuator having a different form, such as a knob or lever, in order to actuate the blade to cut the suture. To this end, the suture(s) can be positioned in a notch, slot, or hole located on the handle, and the actuation of the sharpened blade would cut the suture(s). Upon cutting the suture, a spring or similar component would return the blade to its original position such that the cutting process can be repeated. Alternatively, the cutter can be a simple apparatus such as a static cutting blade located in a narrowing, crevice-like feature on the handle. In this configuration, the suture could be drawn across the sharp edge of the blade in order to cut it. Typical materials that are useful as cutting blades are stainless steel, carbon steel, and gemstones, such as diamond. For safety purposes, the user does not have direct access to the cutting blade; only suture is able to reach the blade via the suture cutter notch or hole. Beyond the safety advantage, the integral cutter would reduce or eliminate the need for the user to provide a separate pair of scissors for cutting or trimming suture during the procedure.

It will be appreciated that the above-described structures constitute exemplary parts of one suturing device according to the present invention and each of these structures is described in greater detail below. The foregoing discussion is thus a brief summary of suitable parts that can be present within the present suturing device; however, are not to be considered to be limiting of the scope of the present invention. The make-up and operation of various exemplary suturing devices in accordance with the present invention are now described.

Certain details of the suture devices are described in commonly owned U.S. patent application Ser. No. 13/584, 536, filed Aug. 13, 2012, which is hereby incorporated by reference in its entirety.

FIGS. 1a-1f show a device 100 according to one embodiment. The suturing device 100 includes a housing 110 that contains a number of the working components and allows a user to easily hold and use the device. For example and as shown in the illustrated embodiment, the housing 110 can be in the form of an elongated handle that is formed of a first part and a second part. The first and second parts are complementary to one another and include a means for attaching the two parts together to form an assembled handle that can be easily grasped and manipulated by the user. For example, the first and second parts can be attached to one another by a mechanical attachment, such as by using fasteners, by establishing a snap-fit between the two parts, etc. The handle 110 not only houses many of the working components but also provides a means for the user to grasp the device 100 but also manipulate it in such a way to cause the needle 101 to be advanced into and through the tissue 10 and then exits the tissue.

Each of the first and second parts is generally hollow and therefore, when the two handle parts are attached to one another, they define a hollow interior handle 110 space that receives and holds many of the working components of the device 100 as will be appreciated below. The first part is an elongated handle part defined by a proximal end (upper end) and a distal end (bottom end) and similarly, the second part is an elongated handle part that is defined by a proximal end (upper end) 122 and a distal end (bottom end) 124. The handle can include ergonomic gripping regions/surfaces 109 suitable for both left and right-handed users to facilitate grasping of the device. As shown, these gripping regions 109 can be in the form of locally recessed and contoured portions of the handle that locate and permit a user's thumb/fingers to grasp the exterior of the device. The gripping regions can alternatively be defined by a modified exterior surface of the housing parts within local handle sections that allow the user to more easily grasp the handle. For example, the exterior surface of the handle can be a rough surface defined by surface features, such as a plurality of raised bumps or the like or can even be defined by a material that is different than the material of the handle and is applied thereto (e.g., a gripping surface member applied to the handle by means of an adhesive or over-molding process or other suitable process).

As shown in the Figures and described in detail herein, the suturing device 100 is configured to move curved suturing needle 101 in a controlled manner such that the suturing needle 101 is advanced into and through target tissue 10 and is then extracted from the tissue to complete one suturing action and allow the user to tie off the suture element itself.

Figure 1C:
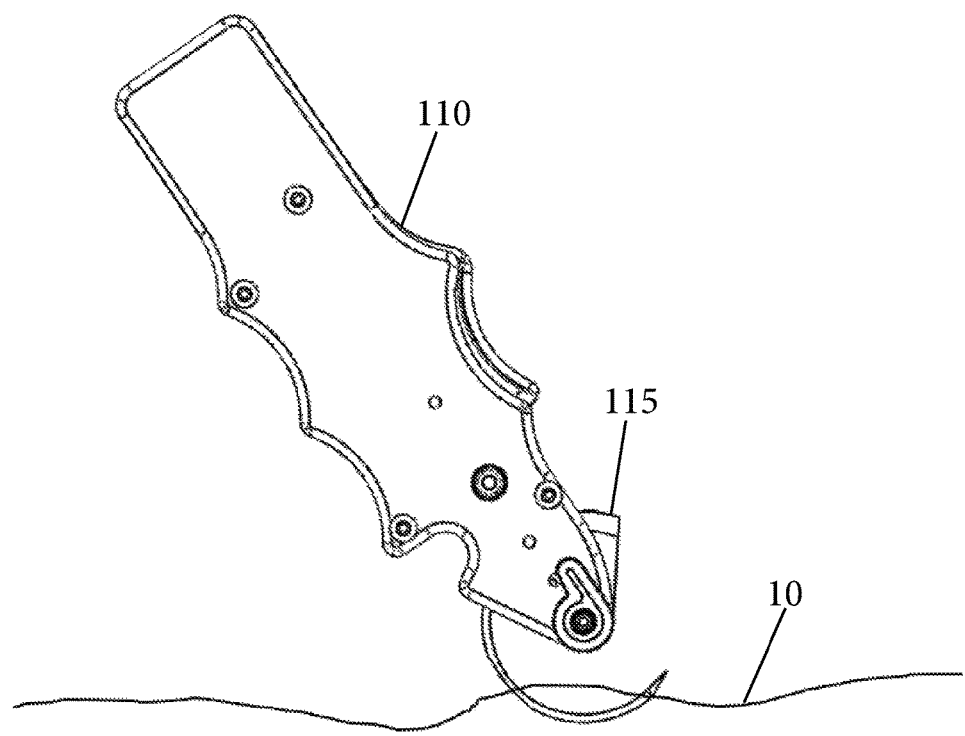
FIG. 1c is a side elevation view of the suture device in a third position.
Figure 1D:
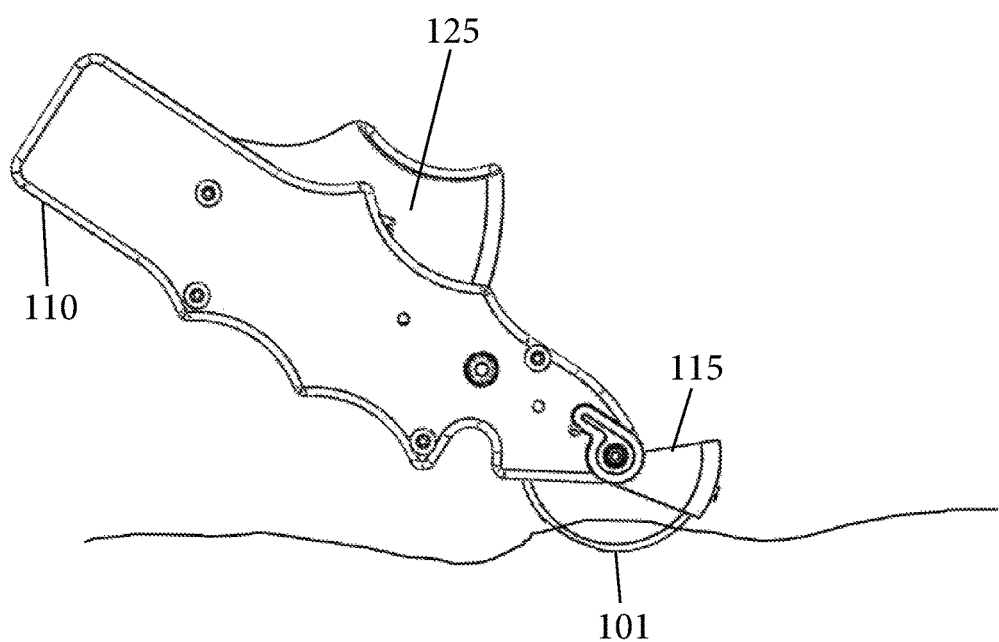
FIG. 1d is a side elevation view of the suture device in a fourth position.
Figure 1E:
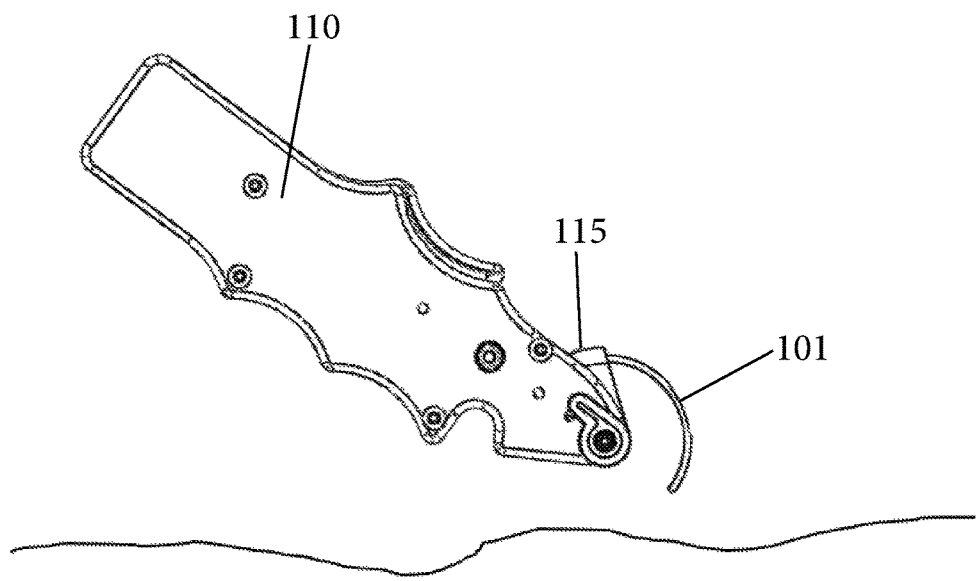
FIG. 1e is a side elevation view of the suture device in a fifth position.
Figure 1F:
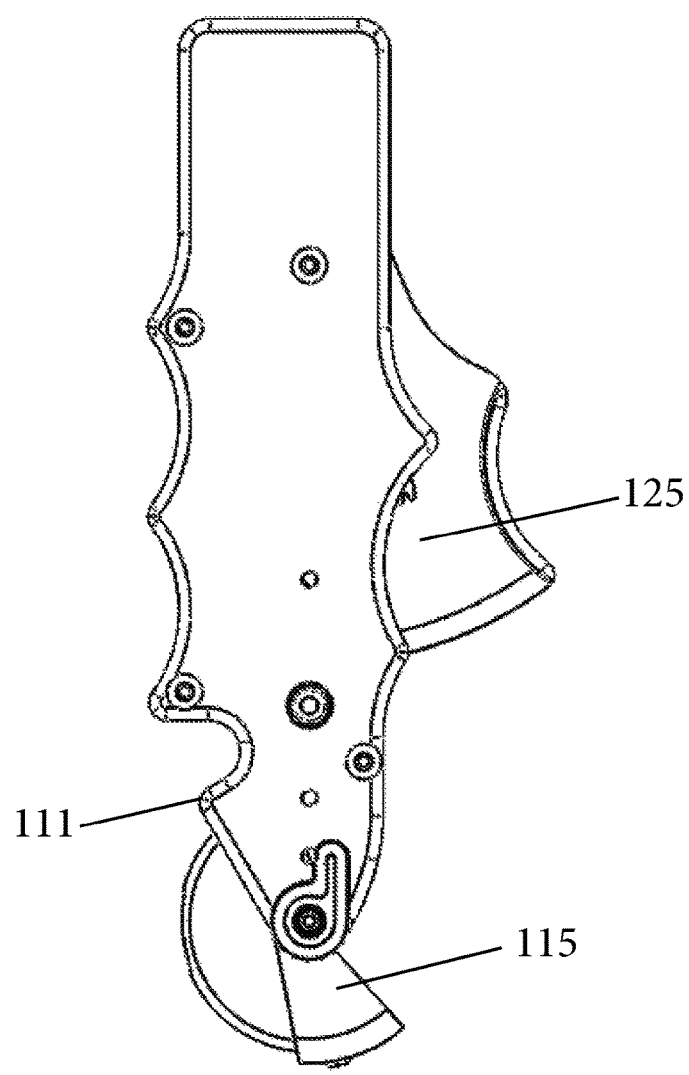
FIG. 1f is a side elevation view of the suture device returned back to the first position.

FIG. 1a shows the suturing device 100 in a first position (rest position) which is a position of the device out of its packaging prior to use. In this first position, a movable gripper (needle capturing device) 115 is in an extended position (6 o'clock position). In this extended position, the movable gripper 115 covers the suturing needle 101. FIG. 1b shows the suturing device 100 in a second position in which an actuator 125 is actuated causing the movable gripper 115 to move to a retracted position in which the gripper 115 is contained in the housing and the needle 101 is exposed and ready for insertion in the tissue 10. The wrist motion is the same as in the '536 application. FIG. 1c shows the suturing device 100 in a third position in which the needle 101 passes through the tissue due to the wrist motion of the user and the sharp end of the needle 101 passes through the tissue 10 and is thereby exposed. In the position, the actuator 125 is still activated (i.e., pressed inward into the housing as shown) and upon release of the actuator 125, the gripper 115 moves back to the rest position and captures and shields the sharp end of the needle 101. In FIG. 1e, the actuator 125 is pressed down (activated) to cause the retraction of the gripper 115 back into the housing, thereby causing the needle to be pulled through the tissue 10. FIG. 1e shows the retraction of the needle 101. FIG. 1f shows the rest position of the needle 101 upon release of the actuator 125.

As mentioned herein, any number of different types of suturing needles can be used with the device. In general, the suturing needle includes a sharp distal end for penetrating the tissue and an opposite proximal end, which is typically a blunt end.

The device also includes an actuator assembly that is used to operate the device and to effectuate the controlled movement (shuttle action) of the suturing needle. The actuator assembly includes an actuator body that is accessible to the user and is manipulated by the user to cause controlled movement of the suturing needle. In the illustrated embodiment, the actuator body extends from the side of the handle and is accessible by the user. The actuator body is operatively coupled to other parts of the actuator assembly to cause the desired controlled movement as described hereinbelow and in particular, causes needle transfer to effectuate the suturing action.

It will be appreciated that the illustrated actuator assembly is merely one exemplary type of actuator that can be used in the present device to cause controlled movement of the suturing needle and there are a number of other actuator assemblies that can be used for causing the needle to be transferred (shuttled) in the manner described herein. For example, while the actuator body is pivotably rotated by the user (e.g., as by pressing the body into the handle), other actuators suitable for use in the present invention can be activated by other techniques, such as pressing a button, rotating an actuator element, etc.

The needle transfer mechanism is comprised of two primary sub-mechanisms: a first gripping mechanism 111 and the second gripping mechanism 115. The first gripping mechanism firmly holds the needle and allows the user to penetrate tissue and also to receive the needle from the second gripper in order to deliver additional sutures. The second gripping mechanism serves to cover the sharp distal end of the needle while the device is in its packaged and reset condition, and also to actively extract the needle from tissue. The first gripping mechanism is generally stationary within the handle while the second gripping mechanism is generally movable relative to the first gripping mechanism and handle. In the illustrated embodiment, the actuator body extends from the side and is connected to a needle transfer mechanism, which as mentioned herein, is designed to controllably move the needle from one operating position to another operating position and more specifically, to transfer the suturing needle from one needle gripping mechanism to another needle to allow the suturing needle to be extracted from the tissue once it passes therethrough.

The general operation of the device is thus depicted in FIGS. 1a-1f. Please note that not all features, i.e., suture cutters, depth controllers, safety apparatus, are shown in these Figures. They are presented in separate Figures and in the detailed description.

FIG. 1a shows the device in its packaged condition with the first gripping mechanism 111 having a firm grasp of the blunt end of the needle 101. The needle point is covered by the second gripping mechanism 115 and is exposed when the user depresses the actuator 125. The user can now penetrate the patient's tissue with the needle by orienting the handle 110 such that the needle point is generally perpendicular to the tissue 10 as seen in FIG. 1b. Once the needle is properly oriented, the user rotates his wrist such that the needle penetrates and exits the tissue as presented in FIG. 1c. When the needle exits the tissue, a safety guard (not shown) surrounds the needle point and protects the user from injury. FIG. 1d depicts the second gripping mechanism 115 capturing the pointed end of the needle when the user releases the actuator 125. With the needle now gripped by the second gripping mechanism, the user can depress the actuator in order to actively extract the needle from the tissue as seen in FIG. 1e. Finally, in FIG. 1f the user releases the actuator and the needle is rotated back to its origin, allowing the user to repeat the suture delivery process. The user may also activate the integral suture cutter (not shown) to cut the suture to length or to trim the knotted suture.

Figure 2A:
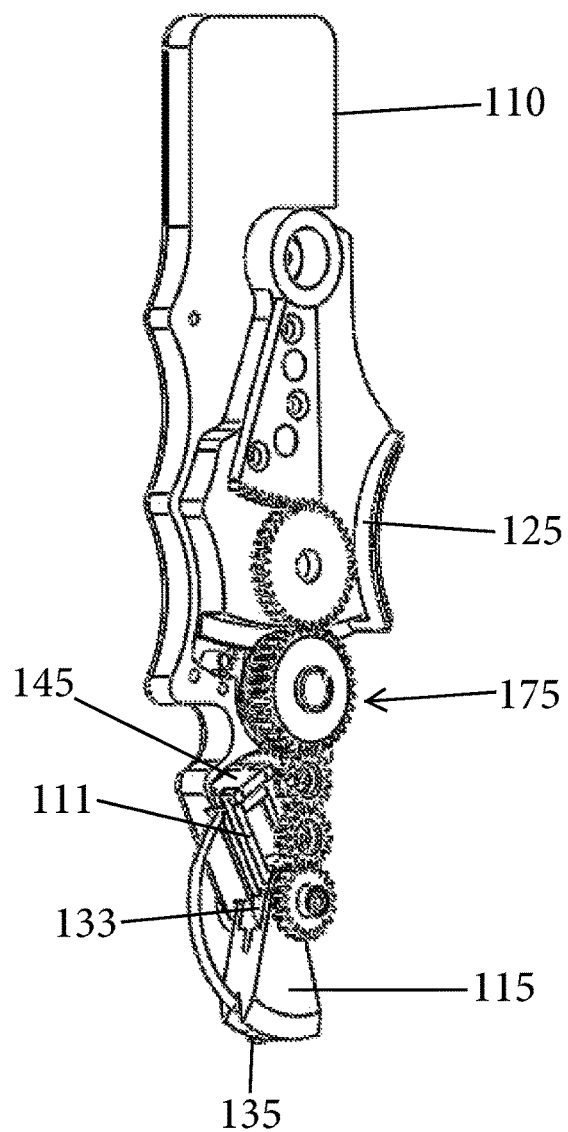
FIG. 2a is a perspective view of internal working components of the suture device.
Figure 2B:
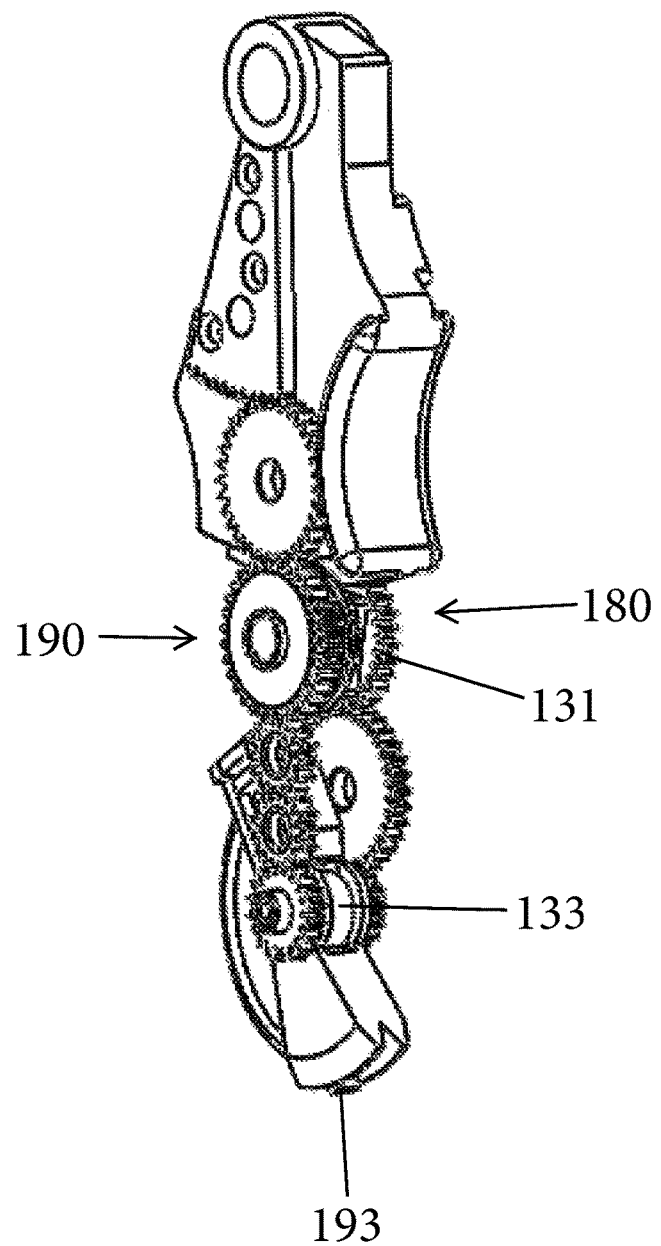
FIG. 2b is a perspective view of an exemplary drive mechanism of the suture device.

In a preferred embodiment the device is provided sterile in sterile packaging, such as a blister pack. The device comes out of the package in an at-rest condition where the needle is gripped by the first gripping mechanism near the distal end of the device, and the second gripping mechanism is in its at-rest position enclosing the distal end on the needle, but not gripping the needle. The needle features a length of suture from its mid-section. FIGS. 2a and 2b show the inner components and mechanism of the preferred embodiment.

In a preferred embodiment the actuator 125 protrudes from the side of the housing 110 and swings in an arcing motion from a first at-rest position to a mechanically limited end-of-travel second position inside the housing when squeezed by the user. A return spring pushes the actuator toward the at-rest position and offers resistance to the user when squeezing.

The actuator 125 is connected to a second gripper 115 by mechanical means (gears, linkages or other means known to the art) such that when the actuator moves from its at-rest position to its fully squeezed position, the actuator 125 moves proportionally from its at-rest position to its fully retracted position.

The actuator is also connected (by gears or other means) to an energy storage device as shown in FIG. 3. In a preferred embodiment, this energy storage device is a torsion spring. (Other embodiments use other kinds of springs, air compressing pistons, fly wheels, opposing magnets or any other energy storage means known to the art.) In a preferred embodiment the torsion spring is wound-up one quarter turn by a gear segment attached to the actuator when the actuator is squeezed, and is latched to hold the stored energy of this quarter turn when the actuator 125 reaches its fully squeezed position. The latch holds the spring in this wound-up condition until the actuator is fully released to its at-rest position, at which time the latch releases the energy of the spring and the spring turns one quarter turn in the un-wind direction.

In FIGS. 2a and 2b, the rear gear train 180 includes the drive gear 131 and is configured to drive the movable second gripper 115 between the extended and retracted positions. A front gear train 190 that includes the windup mechanism 175 of FIG. 3 serves as a mechanism for storing energy when the actuator 125 is depressed and then upon release of this energy, the operating state of both grippers 111, 115 are changed (i.e., changed between a locked, needle capturing position and un-locked, needle receiving or needle releasing position). Thus, the operation of actuator 125 not only causes direct movement of the second gripper 115 between the retracted and extended positions but also causes the two grippers 111, 115 to move between open and closed positions, thereby allowing the needle to be securely held or released.

In a preferred embodiment the energy storage device is further connected to a drive gear by a ratcheting connection such that the drive gear only turns in one direction when the energy in the torsion spring is released. This drive gear is further connected to a rotating cam 133 by a 2:1 gear ratio such that when the spring driven gear moves one quarter turn, the cam moves one half turn. The cam is deployed such that it engages needle clamps of the first gripping mechanism 111 and second gripping mechanism 115 such that every half turn it switches the condition of the two clamps. In one state the first gripping mechanism clamp grips the needle and the second gripping mechanism clamp has released the needle, and in the other state the first gripping mechanism clamp has released the needle and the second gripping mechanism clamp grips the needle.

In use of the preferred embodiment device, the user removes the device from its sterile packaging in its at rest position with the needle tip enclosed by the second gripping mechanism and the proximal end of the needle gripped by the first gripping mechanism clamp. The user then grips the device. In a preferred embodiment, the user grips the device between his/her thumb and one or more fingers with the user's thumb on the actuator.

The user then squeezes the actuator, retracting the second gripping mechanism, exposing the needle tip, and winding-up the energy storage device.

The user then positions the needle tip against the tissue to be sutured and passes the needle tip through the tissue by rotating the housing in an arcing motion until the needle tip emerges from the tissue.

Next, the user slightly releases his grip on the actuator, allowing the return spring to move the actuator into its initial at-rest position, and, in so doing, rotates the second gripping mechanism to re-engage the distal tip of the needle. When the actuator reaches the end of its stroke at the at rest position, the latch releases the wound-up torsion spring energy in the energy storage device, causing the drive gear to rotate one quarter turn, and through the 2:1 gearing, the cam to turn one half turn, thereby switching the state of the clamps such that the first gripping mechanism clamp is now released and the second gripping mechanism clamp grips the distal end of the needle.

Next, the user re-squeezes the actuator. The second gripping mechanism, now gripping the needle, rotates from the at-rest position to the retracted position, and in so doing, actively and rotationally extracts the needle from the tissue. The actuator movement also winds-up the energy storage device for its next action.

Still squeezing the actuator, the user lifts the device from the tissue, pulling a length of suture through the tissue. The user then releases his/her grip on the actuator, allowing it to rotate back to the at-rest position, and in so doing rotating the second gripping mechanism to its at rest position, releasing the stored spring energy in the energy storage device, rotating the drive gear and the cam, and switching the state of the clamps to its original condition where the first gripping mechanism clamp grips the proximal end of the needle and the second gripping mechanism clamp has released the needle, yet still covers the needle.

Finally the user ties the suture to form a stitch and trims the suture near the knot, leaving the user holding the device in exactly the same condition as when it was removed from the package, except for a slightly shorter length of suture. The device is now ready to deliver additional sutures.

Now referring to FIG. 4, looking specifically at the first gripping mechanism 111, it includes a body 141, a clip 143 and a toggle block 145. The toggle block 145 and the body 141 operate together to grip and release the needle. The body 141 is generally fixed to the handle and is hinged to the toggle block 145. The clip is also hinged to the toggle block 145. A biasing means such as a spring, connects the clip 143 to the cam shaft 161 and aids the mechanism to move from a needle gripping condition to a needle releasing position. The spring is held between ledges of the body 141 and clip 143 and thus applies a biasing force to the movable clip 143.

Cam 195 disposed about the shaft 161 selectively strikes the biased clip 143 and when the cam is in the high position and contacts the clip 143, it causes the clip 143 to move away from the shaft 161 resulting in plate 145 pivoting open (allowing needle to enter or exit). Conversely when the cam is in the low position and does not drive the clip 143, the spring biases the clip 143 closed resulting in the toggle plate 145 being in the closed position, thereby locking the needle.

Protrusions 149 serve as a means for locking the body 141 in place relative to the housing 110 and maintain it in a fixed position for the first gripper 111.

The toggle block 145 acts as a lever and therefore transmits a higher gripping force, which is necessary to support the needle as it penetrates tissue. It will be appreciated that the shape of the notch in the body 141 and the concave shape of the clip 143 provide an effective gripping interface between the two at the location at which the two are in intimate contact. For example, the interface is defined between the V-shaped notch and the needle portion which can have a trapezoidal shape, thereby creating a matched fit between the two structures. It will be appreciated that the shapes of the notch and needle can be different, i.e., round, oval, hexagonal, so long as preferably there is the above-described match fit between the two resulting in an effective needle gripping location. The shape of the needle also facilitates the intimate engagement between the pin and the needle since a face (e.g., a flat surface) of the toggle block 145 can intimately contact a complementary face (e.g., a flat surface) of the suturing needle, thereby securely holding the needle in the respective channel.

As with the first needle gripper body, the second gripping mechanism 115 has an open bottom to allow the clamp pin 193 contained therein to be in intimate contact with the cam member and the body has an opening formed in the notch that allows passage of the pin therethrough. Unlike the first gripping mechanism 111, the second gripping mechanism 115 is a movable gripper that can move to different positions and in different directions as described herein. This arrangement allows the second gripper 115 to rotate relative to the cam shaft 161 upon activation of the actuator and in particular in response to movement of the actuator body. As a result of the above arrangement and mechanical coupling of parts, the inward and outward movement of the actuator body causes a pivoting of the second gripping mechanism about the cam shaft.

Figure 5:
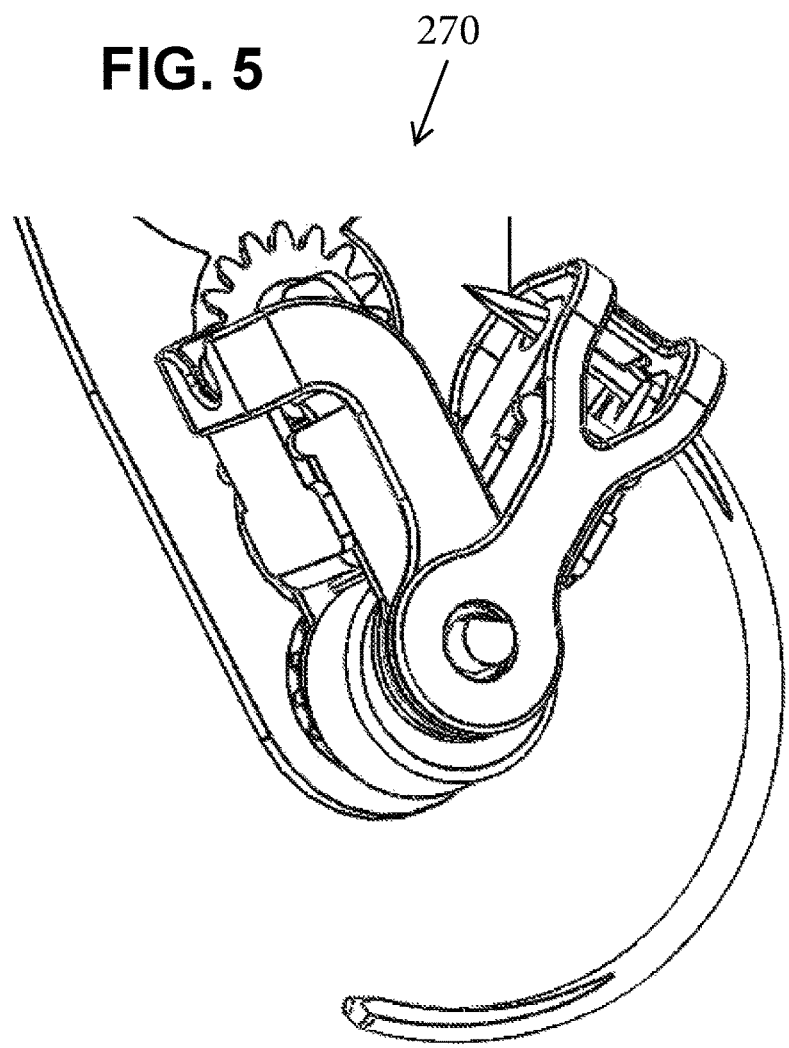
FIG. 5 is a perspective view of a distal end of the suture device.
Figure 6:
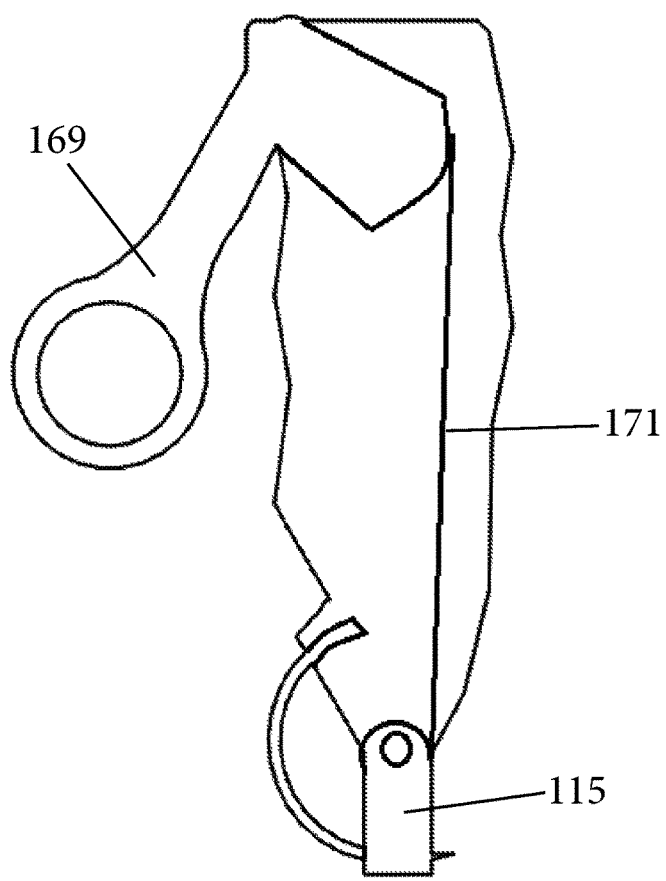
FIG. 6 is a side view of a side actuator based suture device according to the present invention.

Alternative methods of rotating and gripping a first or second gripping mechanism are seen in FIGS. 5 and 6. In both cases cams create the reciprocating grip and release operation. In one case a cable is used to exert rotation upon the second gripping mechanism 115. FIG. 5 shows another type of clamp mechanism 270. In FIG. 6, a pulley mechanism with cable 171 is used and operatively connected to the actuator 169 which can contain a thumb loop for causing activation of the pulley mechanism. The winding and unwinding of cable 171 causes the second gripper 115 to move between the extended and retracted positions.

The safety shield mechanism (FIG. 12) is configured to shield the suturing needle 101 during the operation of the device and the controlled movement of the suturing needle 101, thereby protecting the user from undesired contact with the suturing needle 101. In the illustrated embodiment, the safety shield mechanism 600 is formed of a pair of safety shields 610, 620 that are freely movable relative to the handle and are positioned and constructed such that as the suturing needle 101 is advanced into the tissue 10 and then subsequently exits the tissue 10 and is captured by the needle transfer mechanism 400, the safety shields 610, 620 shield the sharp end 103 of the suturing needle 101. Each safety shield 610, 620 can be in the form of a safety shield member (structure) or can be in the form of a shied assembly formed of several parts that in combination shield the needle 101 and move in the manner described herein.

The safety shields 610, 620 are preferably biased so as to assume the desired position as the device 100 is used in the manner described herein. More specifically and according to one exemplary embodiment, the safety shield 610 has a structure that surrounds the suturing needle 101 so as to prevent easy, direct access thereto. The illustrated safety shield 610 includes a pair of side supports with a bottom support extending therebetween and containing an opening (slot or notch) to permit the suturing needle 101 to pass therethrough as the suturing needle 101 moves relative to the safety shield 610. As shown, the safety shield 610 is preferably a simple structure and therefore, the side supports can be substantially hollow and include openings formed therein. The bottom support also serves to space the two side supports apart from one another.

The safety shield 610 is biased with a biasing member, such as a spring, to thereby direct the safety shield 610 to an initial rest position by means of the biasing force. However, when a sufficient force is applied to the safety shield 610, the biasing force is overcome and the shield can be moved in the other direction. For example, when the safety shield 610 is brought into contact with the tissue 10, the contact with the tissue drives the safety shield 610 against the biasing force.

The illustrated safety shield 620 includes a pair of side supports with a bottom support extending therebetween and containing an opening to permit the suturing needle 101 to pass therethrough as the suturing needle 101 moves relative to the safety shield 620. As shown, the safety shield 620 is preferably a simple structure and therefore, the side supports can be substantially hollow and include openings formed therein. The bottom support also serves to space the two side supports apart from one another. In one embodiment, a tab can be provided between the side supports and serves to block contact with the sharp end 103 of the needle 101. The tab represents a physical structure that lies adjacent the sharp end 103 and thus effectively blocks the user from lateral access to the sharp end 103.

In one embodiment, at least one of the safety shields 610, 620 rotates relative to the handle (e.g., the cam shaft 340) when the device 100 is pressed with sufficient force against the patient's tissue. During the operating state of the device 100 when the device 100 and the safety shield mechanism 600 are rotated, the suturing needle 101 is progressively and safely exposed such that it can penetrate the patient's tissue 10. The various positions of the suturing needle 101 and safety shield mechanism 600 are described in more detail below. In the illustrated embodiment, the second shield 620 also rotates relative to the handle and relocates to the needle exit location of the patient's tissue 10 in order to protect the user from the sharp end 103 of the needle 101.

Each of the illustrated first and second safety shields 610 is biased with a biasing member, such as a spring, to thereby direct the safety shield 610 to an initial rest position by means of the biasing force. However, when a sufficient force is applied to the safety shield 610, 620, the biasing force is overcome and the safety shield(s) moves.

The shields 610, 620 are merely exemplary and the shields can take any number of different forms so long as they perform the intended function. For example, the shields can be constructed from a frame-work of formed wire or plastic and can be formed of one or more components and its rotation may be constrained by a spring or other suitable means as shown. Further, the spring element may be integral to the framework, e.g., a wire form constructed of spring tempered steel or nickel titanium alloy which possess substantial elasticity. It features a spring bias that predisposes the shield towards covering the needle point when the device is in its ready to penetrate configuration.

Figure 8:
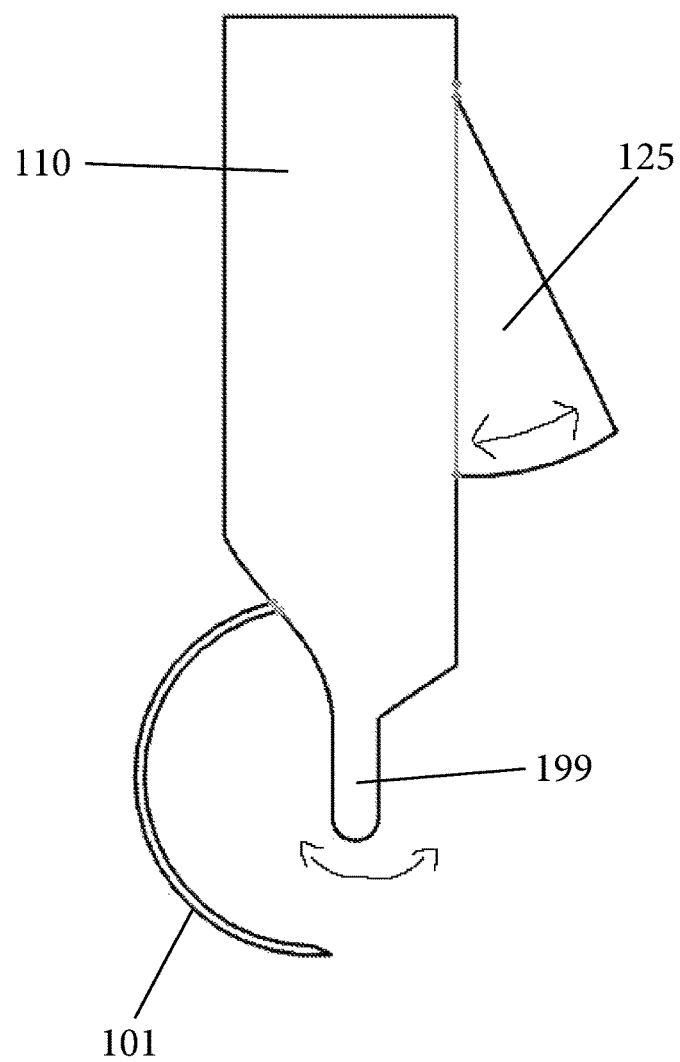
FIG. 8 is a side view of a side actuator based suture device according to the present invention.
Figure 9:
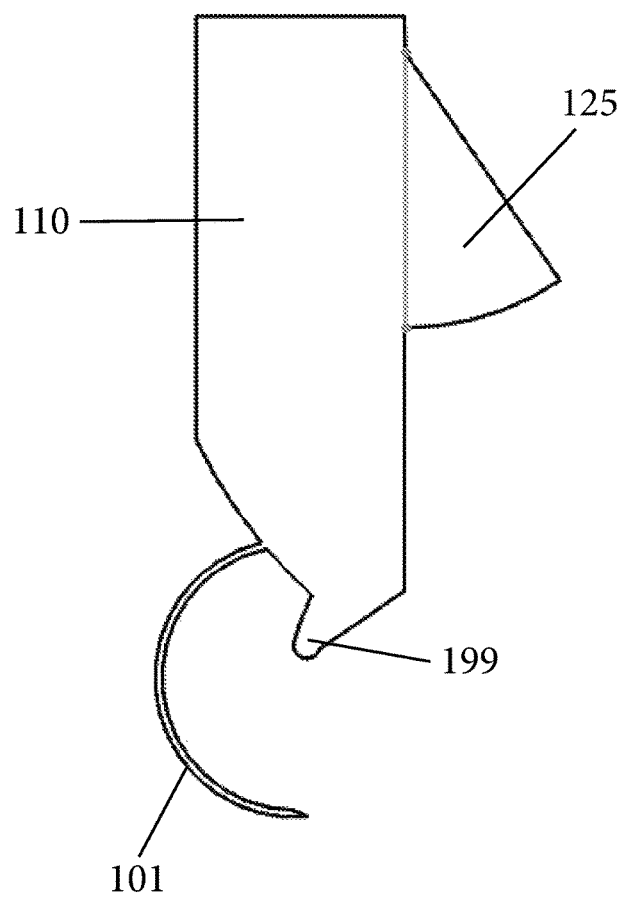
FIG. 9 is a side view of a side actuator based suture device according to the present invention.

As seen in FIGS. 8 and 9, the distal tip 199 of the housing may also be designed in a specific geometric manner such that it predetermines the needle trajectory through the patient's tissue. The tip, when placed on the tissue, would guide the user's rotational hand motion such that the needle would initially penetrate the tissue in an essentially perpendicular orientation and is subsequently oriented into a more obtuse orientation that facilitates the advancement of the curved needle through the remaining tissue. In one embodiment the tip is semi-rigidly angled to create this orientation and in a second embodiment the tip is semi-flexible and creates this orientation. This gentle compound rotating motion is representative of that which is currently employed by healthcare personnel when manually driving needles through tissue. In practical terms, it minimizes the risk of excessively penetrating the patient's tissue.

Finally, a suture cutter (FIGS. 10 and 11) that is integral to the handle would provide the user with a means to cut and trim suture during the procedure. The cutter is an internal dynamic shearing apparatus, i.e., scissors or slideable blade(s) that would require the user to press or slide a button 200 in order to activate a blade 210 to cut the suture. The button 200 is connected to a means that translates the blade 210 across the suture and into a slot 211 that is functionally narrow, providing a holding surface for the suture and allowing only the blade 210 to travel therethrough. This means could be a slideable track if the button were to slide in the direction of the blade 210, or a pair of matched ramps that would convert the vertical motion of the depressed button to a horizontal motion of a cutting blade. A spring or other suitable means (not shown) would return the button 200 to its original position. Further, the suture would be positioned in a notch, slot, or hole on the outer surface of the housing 110 in order for the user to cut it.

Figure 7:
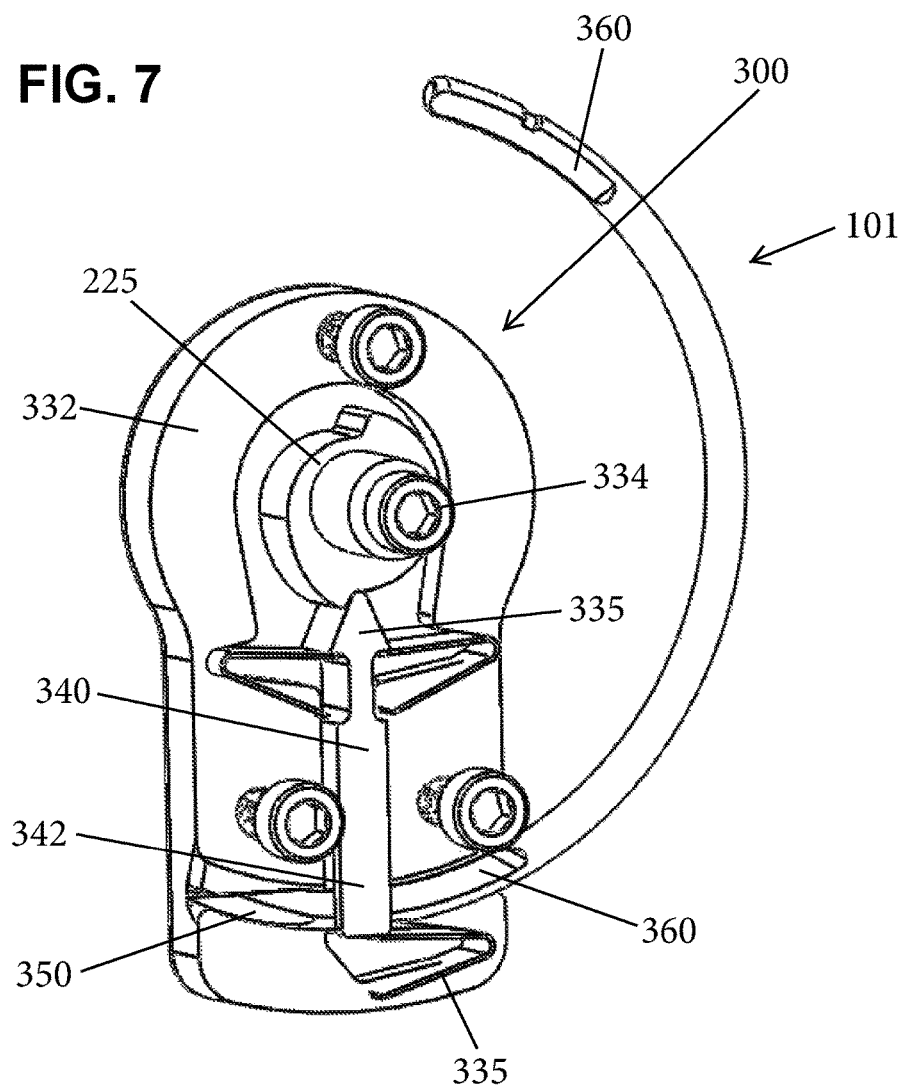
FIG. 7 is a perspective view of a needle capturing component.

FIG. 7 shows an alternative needle gripper design 300. The gripper 330 includes a body 332 that has a rotatable shaft 334 that carries a cam 336. The gripper 330 also includes a movable (translatable) link 340 that moved linearly within a track formed in the body 332 and as a pointed end 335 that is in contact with the cam 336. The body 332 includes a needle receiving slot 350 that can have a curved shape to accommodate the arcuate movement of the needle 101. The link 340 has two bottom leg portions 342 that are spaced apart such that a slot or opening is formed between the leg portions 342 for receiving the needle 101. The needle 101 thus travels between the leg portions 342 and does not contact the leg portions 342.

Within the body 332, a spring clip 335 is disposed and the one leg of the spring clip 335 serves to lock the needle 101 within the slot 350 by being received within a notch 360 formed in the needle 101 (the needle 101 has two notches 360 one at each end for selectively locking each end of the needle 101). The spring clip 335 is in contact with the leg portions 342 of the link 340 and thus the linear motion of the link 340 either causes the spring clip 335 to store energy or allows it to release energy. In particular, rotation of shaft 334 cause rotation of the cam 336 and depending upon the state of the cam 336, the cam 336 either drives the link 340 toward the clip 335 thereby causing the clip 335 to compress and store energy and be released from the needle notch 360 (thus allowing the needle 101 to move within the slot 350). In other positions, the cam 336 does not drive the link 340 downward and the spring clip 335 is in the rest position (stored energy released) and is received in notch 360, thereby locking the needle 101 in the slot 350.

FIGS. 13A through 15F depict an alternative and preferred embodiment of the present invention. The figures illustrate a suturing device with specific mechanisms for clamping a needle, passing a needle through tissue, extracting the needle from the tissue, and returning the needle two its original location for additional suture stitches. The embodiment of the device features many mechanisms similar to that described above and also includes additional novel mechanisms for accomplishing the goal of allowing a user to safely complete a series of sutured stitches without the possibility of an accidental needle stick injury. These embodiments of the invention are described with the help of multiple Figures, which when taken as whole, represent a preferred embodiment of the present invention.

Figure 13A:
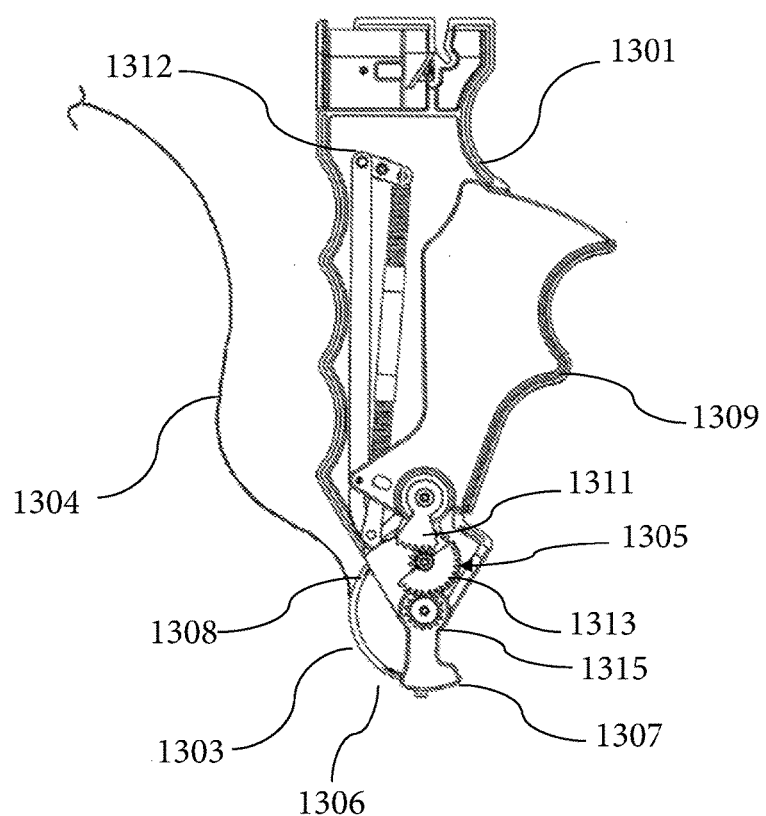
FIG. 13a is a side elevation view of a suture device according to another embodiment showing it in a first position.
Figure 13B:
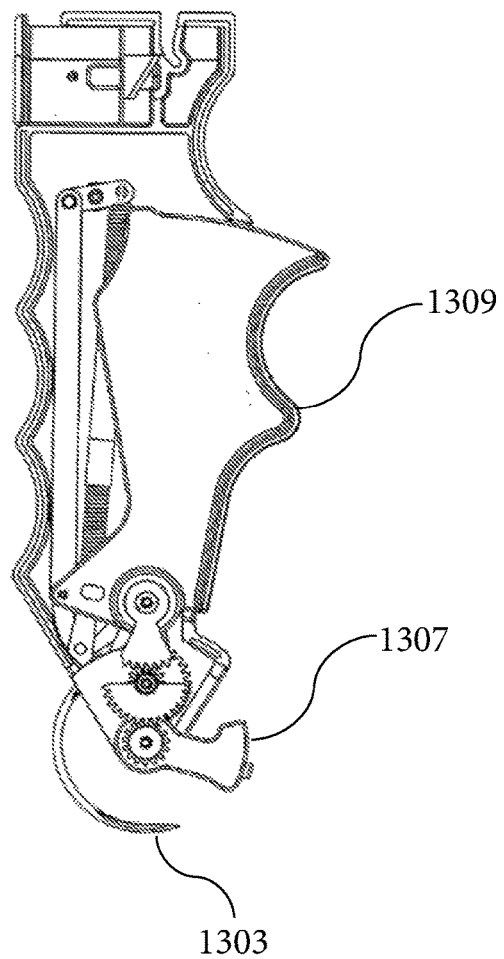
FIG. 13b is a side elevation view of the suture device in a second position.
Figure 13C:
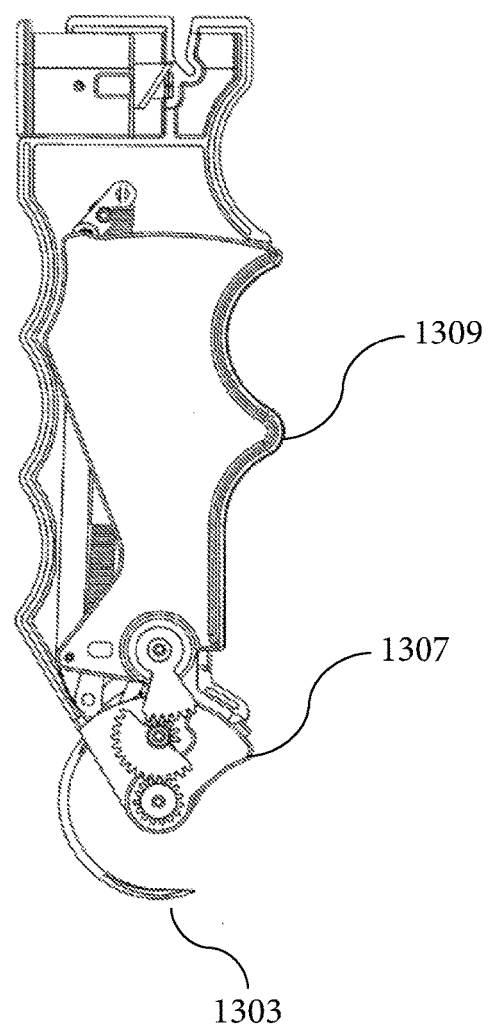
FIG. 13c is a side elevation view of the suture device in a third position.

Turning now to FIGS. 13A-C, an embodiment of the present invention is depicted. The suturing device 1301 of FIG. 13 has two sets of drive mechanisms; the front drive chain (not shown in FIG. 13) controls the clamping and unclamping of a suture needle 1303 while the back drive mechanism 1305 controls the reciprocating rotational motion of the catch arm 1307. For clarity these two sets of drive mechanisms are illustrated separately however, they are driven by the same user action, which is the depressing and releasing of the actuation lever 1309. The back drive mechanism, which is responsible for the rotational motion of the catch arm, is the focus of FIGS. 13A-C.

While the suturing device of FIGS. 13A-C is configured to include the safety shields as described in FIG. 12 and throughout the disclosure, the safety shields are not illustrated in FIGS. 13A-C for the purpose of improving the clarity of the drawings. Additionally, the suturing device of FIGS. 13A-C is illustrated with the suture cutting mechanism as described in FIGS. 10 and 11. Since these cutting mechanisms have been adequately described above they will not be described in detail again here.

FIG. 13A shows the suturing device in the configuration that may be considered the packaged or ready to use configuration. The suturing device is designed to drive through animal tissue a suturing needle 1303 which has a suture material 1304 extending from the needle between the distal 1306 and proximal ends 1308 of the needle. The suturing device consists of a hollow housing, of which the inside of the front half 1312 is visible in FIG. 13A. Pivotably connected to the housing is an actuation lever 1309. The actuation lever includes a gear wedge 1311 which is engaged with a gear-ratio reducing gear 1313. The reducing gear is in turn engaged with a geared surface 1315 on the catch arm 1307. The end result of this gear engagement is that every motion of the actuation lever results in motion of the catch arm. The gear ratio is configured such that one full actuation of the actuation lever results in approximately 150 degrees of rotation of the catch arm. The action of the lever and catch arm is illustrated in FIGS. 13B and 13C.

FIG. 13B shows the actuation lever 1309 roughly halfway depressed. The catch arm 1307 has traveled roughly half way through its travel and the distal tip of the suturing needle 1303 has been exposed.

FIG. 13C shows the actuation lever 1309 fully depressed. The catch arm 1307 has traveled through its full range of motion and the needle point 1303 is fully exposed and ready for insertion into the tissue to be sutured.

Figure 13D:
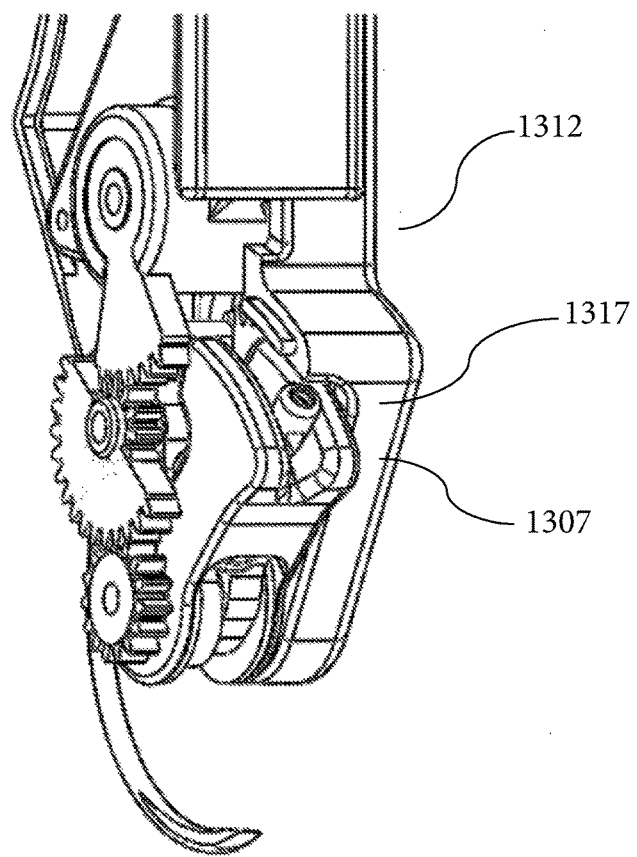
FIG. 13d is a perspective view of a distal end of the shuttle gripper mechanism.

FIG. 13D shows a close up isometric view of the catch arm 1307 in its fully retracted position. The catch arm is configured to collapse into the housing 1312 through a side cavity 1317 at the distal end of the housing.

Figure 14A:
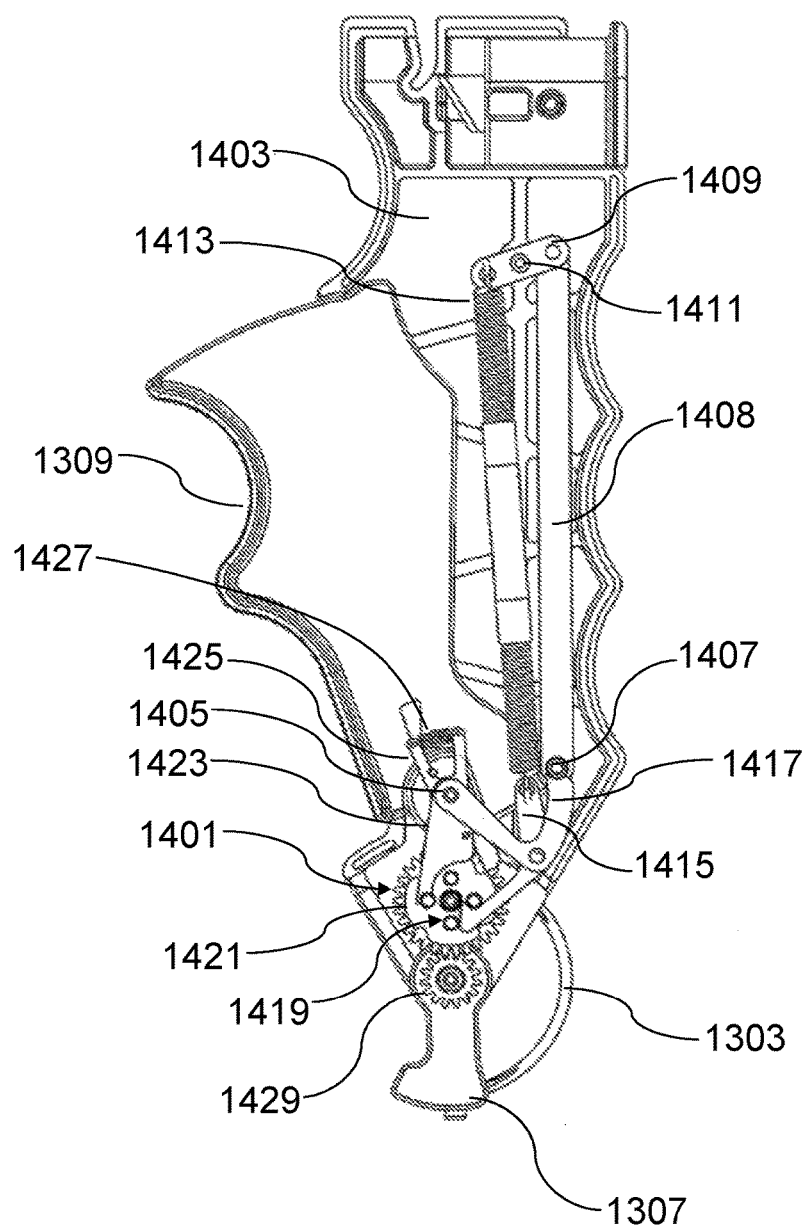
FIG. 14a is a side elevation view of a suture device according to the present invention showing the device in a first position.

Turning now to FIG. 14A, the front drive chain 1401 of suturing device of FIG. 13 is depicted. The front drive chain controls the clamping and unclamping of the suturing needle 1303. The suturing device is shown in the as-packaged or ready to use configuration. The suturing device includes a hollow housing, of which the inside of the back half 1403 is visible. Much like in FIG. 13A the actuation lever 1309 is pivot-ably connected to the housing at the actuation lever pivot point 1405. A shoulder screw 1407 is fixed to one end of the actuation lever and the actuator link 1408 is in turn pivot-ably connected to the shoulder screw. The actuator link connects the actuation lever to the rocker 1409. The rocker is rotationally coupled to the housing at the rocker pivot point 1411. Also connected to the rocker, in a position directly opposite the actuator link is a drive spring 1413. The drive spring in turn, connects to the drive hook 1415. The drive hook engages two mechanisms in the front drive chain, first it is pivot-ably connected to the hook linkage 1417, and secondly the hook engages the series of pins 1419 on the windup gear 1421. The hook linkage shares the pivot point

1405 with the link actuator, and is rotationally fixed about this point. In addition to the hook linkage, the anti-reverse ratchet 1423 and windup release pawl 1425 share a common pivot point about which they are rotationally fixed. The pawl and ratchet are spring loaded relative to each other by the extension spring 1427. The spring load encourages the engagement of the ratchet and the pawl with the windup gear. Alternatively, these components could be separately spring loaded by a feature built into or molded into the housing. Lastly, the windup gear interfaces with the cam gear 1429, which in turn engages the clamping cam (not shown). It is worth noting that the cam gear and the clamping cam are rotationally keyed together. The interaction of the clamping cam with the cam gear will be described in detail later in the disclosure.

The linkages, ratchet, pawl, windup gear and cam gear represent the front drive chain of the suturing device of FIG. 13. The function of the front drive chain is to toggle the clamping and unclamping of the fixed clamp (described in detail in FIGS. 15A-F) and the catch arm 1307. FIGS. 14A-D will show how the motion of the actuator results in the storing of energy from the drive spring, the sudden release of this energy through the windup gear, and the transfer of this energy to the cam gear. Additional Figures will show how the rotation of the cam gear results in the toggling of the clamping status of the catch arm and the fixed clamp. Once the workings of the front drive chain, the back drive chain, and the clamps are understood the working of the device in use can be described in simple terms.

Figure 14B:
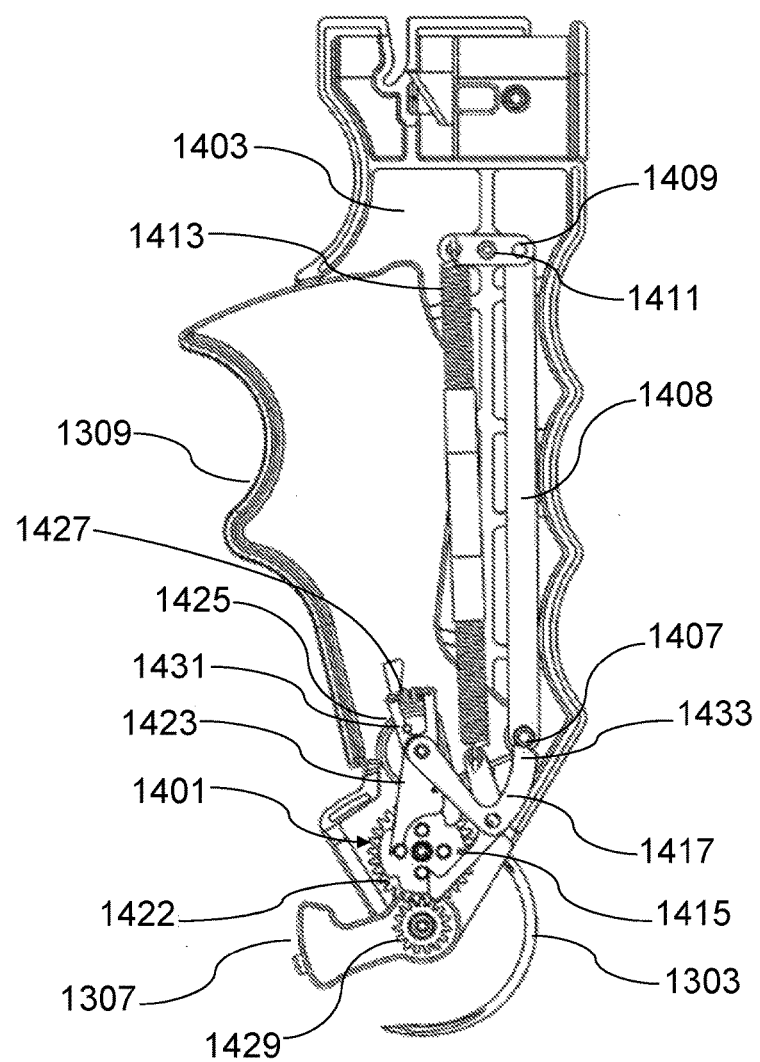
FIG. 14b is a side elevation view of the suture device in a second position.

Turning now to FIG. 14B, the front drive chain of the suturing device of FIG. 13 is depicted, with the actuation lever 1309 half way depressed. The depression of the actuation lever first causes the pawl 1425 to engage the windup gear 1421, preventing counter-clockwise rotation of the windup gear. The engagement of the pawl with the windup gear happens in the first few degrees of the depression of the actuator. The engagement of the pawl is accomplished due to the spring force on the pawl and due to the fact that the pawl release pin 1431 component of the actuation lever is no longer holding the pawl off of the surface of the windup gear. The pawl is capable of engaging the windup gear at four pawl engagement locations, which are depicted as notches 1422 in the windup gear. The four locations are spaced 90 degrees apart on the windup gear, such that after each 90 degree rotation of the windup gear the pawl is capable of engaging the gear. The actuation lever has also pulled down on the actuator link 1408 which has in turn causes the rocker 1409 to pivot and this in turn tensions the drive spring 1413. The depression of the actuation lever further causes the shoulder screw 1407 to hit the proximal arm 1433 of the hook linkage 1417. The engagement of the shoulder screw and the hook linkage helps steers the drive hook 1415 in a direction that roughly follows the circumference of the windup gear. Note that as described in FIGS. 13A-D, the depression of the actuator has caused the catch arm 1307 to retract.

Figure 14C:
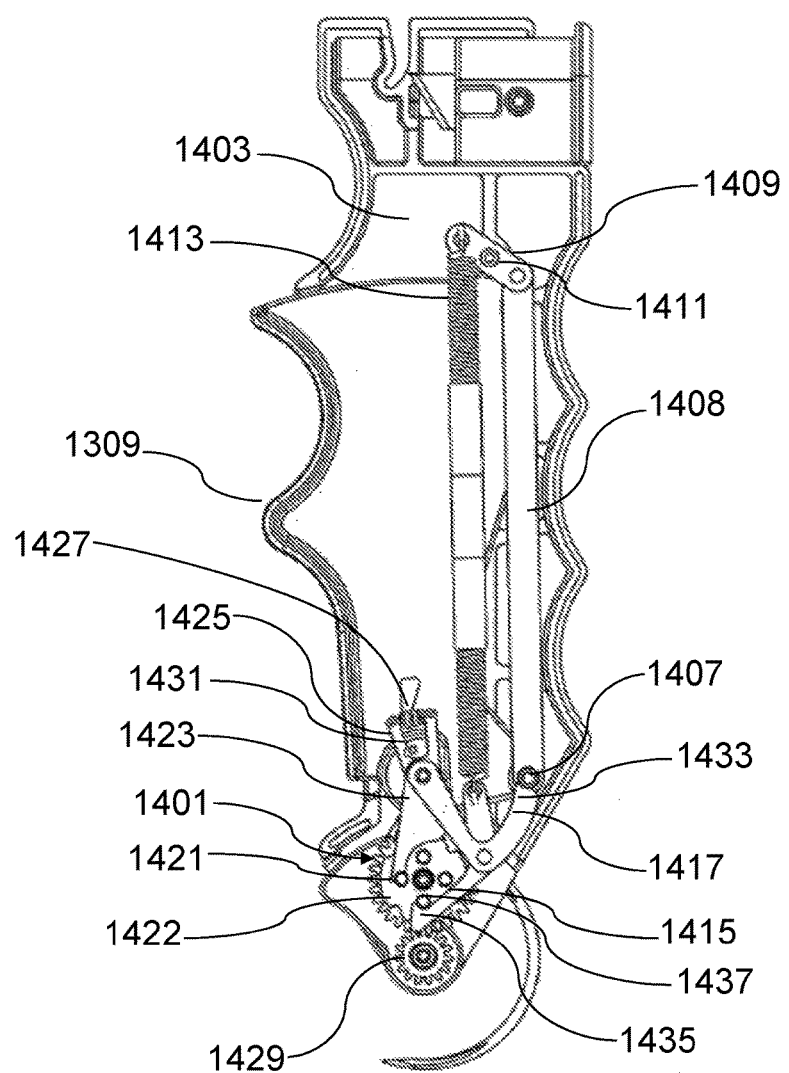
FIG. 14c is a side elevation view of the suture device in a third position.

Turning now to FIG. 14C, the front drive chain of the suturing device of FIG. 13 is again depicted, with the actuation lever 1309 fully depressed. The pawl 1425 is still engaged with the windup gear 1421. The additional actuation of the lever has further depressed the actuator link 1408 which has further pivoted the rocker 1409 and further tensioned the drive spring 1413. The shoulder screw 1407 which is connected to the actuator and the actuator link has further pushed on the proximal arm 1433 of the hook linkage 1417. The motion of the hook linkage has caused the drive hook 1415 to further rotate. The distal hook feature 1435 of the drive hook has snapped into engagement with the windup gear pin 1437. Once again, as described and illustrated in FIG. 13, the catch arm has moved into its cavity in the shell. It should be noted that at this point the windup gear has not moved at all and therefore the cam gear 1429 hasn't moved either. Instead of moving the windup gear the depression of the actuator has engaged the drive hook with the windup gear pin and has spring loaded the drive hook with a significant spring force.

The device as illustrated in FIG. 14C is now in the primed position. The user would drive the needle through the tissue to be sutured using the normal wrist pronation needle driving technique. The shields (not shown in FIG. 14 for clarity) would protect the user from accidental needle sticks at this time. The user is able to penetrate the tissue with the needle only for as long as the actuation lever is held depressed. If the user releases the actuation lever the catch arm returns to its home position and covers the tip of the needle.

Assuming the user has thrown a stitch and is satisfied with the suture placement, the user would begin releasing the actuation lever. During the release of the lever the front drive train remains fixed in the position illustrated in FIG. 14c until the very end of the release stroke of the actuator. The reason for this is that the drive hook is engaged on the windup gear pin, and the anti-reverse ratchet and the pawl combine to prevent motion of the windup gear in either the clockwise or the counter-clockwise direction. During the return stroke of the actuation lever, the back drive train returns the catch arm to its initial packaged position, covering the distal end of the suture needle 1303. The front drive train remains spring loaded until the very end of the actuation lever return stroke. At this point the pawl-pin 1431, which is essentially a protrusion on the actuation lever, contacts the pawl and disengages the pawl from the windup gear. Now the spring tension that was built up during the actuator depression is released. The drive hook returns to its original position, causing the windup gear to rapidly rotate counter-clockwise 90 degrees. This rotation causes the cam gear to rotate 180 degrees due to the 2:1 ratio of the cam gear and the windup gear. The front and back drive trains have now returned to their original packaged positions, with the exception that the cam gear has rotated 180 degrees, which has in turn rotated the cam (to be described in FIGS. 15A-F) 180 degrees.

In order to recap, FIGS. 13A-D and 14A-C have shown that a complete actuation cycle of the actuation lever causes the catch arm to shuttle backwards and forwards and also causes the cam gear to rotate 180 degrees. Furthermore, the timing of the motion of the catch arm and the cam gear has been shown such that catch arm completes its reciprocating rotation before the cam gear begins its spring driven rotation.

Figure 15A:
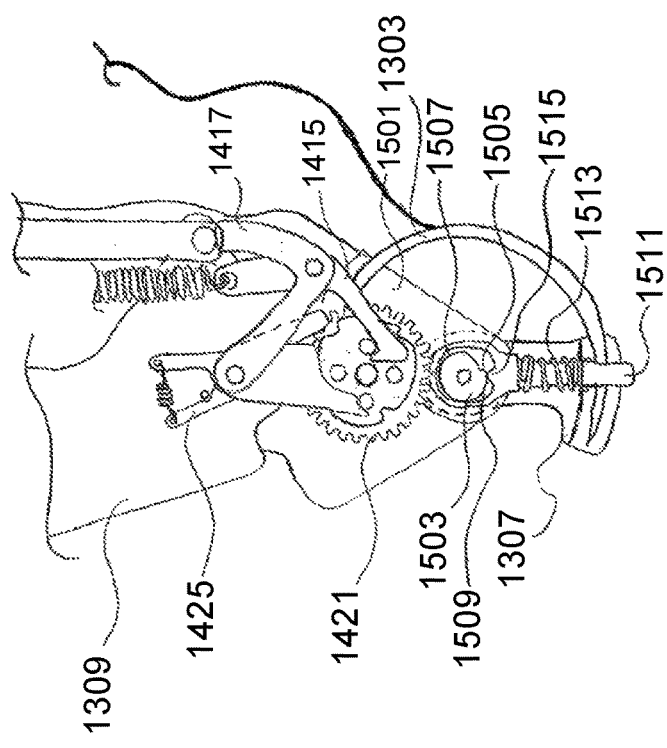
FIG. 15a is side elevation view of distal end of the suture device.

Turning now to FIG. 15A, a close-up view of the distal end of the suturing device of FIGS. 13 and 14 is depicted. Much like FIG. 13A, the suturing device of FIG. 15A is shown in the as-packaged or ready to use configuration. In order to illustrate the needle clamping and un-clamping action of the catch arm 1307, the fixed clamp 1501, and the cam 1503 some of the other components of the suturing device have been hidden. Specifically, the cam gear has been hidden as well as the front of the case of the suturing device. The actuation lever 1309, drive hook 1415, hook linkage 1417, pawl 1425, and windup gear 1421 assembly of FIG. 15 is configured to work as described above. The cam is configured to rotate about the same pivot point that the catch arm pivots about. The cam is further configured such that it is rotationally coupled to the cam gear (not shown, described above). The cam features a surface with two distinct diameters and a short transitional section 1505 between the two diameters. The smaller diameter of the cam 1507 may be configured to be about 0.030" smaller than the larger diameter of the cam 1509. The shuttling catch arm, described above, is shown with a clamping pin 1511 which is spring-loaded by the clamp spring 1513. The clamping pin further includes a cam follower 1515 which rides along the surface of the cam. The clamping pin has an elongate hole (not shown) through which the suture needle 1303 may enter and exit as determined by the workings of the device. The catch arm clamping pin is depicted in FIG. 15A in a configuration such that the catch arm is not clamping the needle. The fixed clamp is shown partially obscured by the workings of the device; however, the action of the fixed clamp is the same as the catch arm except that the fixed clamp does not move during the use of the device. The fixed clamp also features its own clamping pin (not shown) and which is also spring loaded by a clamp spring (not shown) and which also includes a cam follower (not shown). The clamp pin of the fixed clamp of FIG. 15A is currently clamping on the needle, thereby preventing the needle from moving relative to the fixed clamp.

Figure 15B:
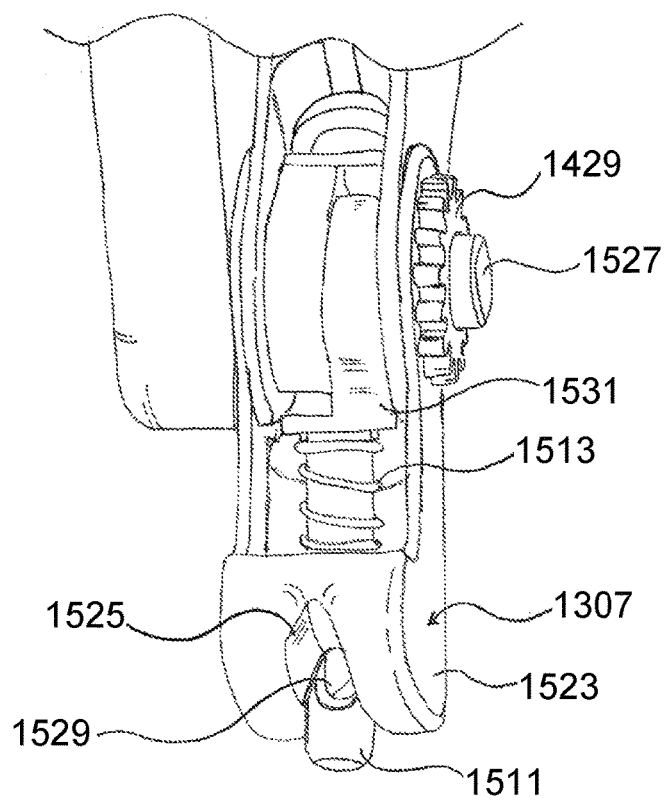
FIG. 15b is a perspective view of the distal end of the suture device.

FIG. 15B shows a close up side view of the needle clamping mechanism of the catch arm 1307. This same needle clamping mechanism is employed by the fixed clamp 1501. While the suturing device of FIG. 15 includes a hollow housing with a front half and a back half, only the back half of the housing 1521 is shown in FIG. 15B. The catch arm assembly 1307 includes a catch arm housing 1523, which features a circular surface with a v-notch 1525 cut into it. The catch arm housing pivots about the catch arm pivot point 1527. A clamping pin 1511 resides inside a hole in the housing and is spring loaded against the housing by the clamp spring 1513. The clamping pin includes an elongate clamping pin hole 1529. The clamping pin also includes a yoke 1531 which encases the cam (not shown). The cam is rotationally coupled with the cam gear 1429. Both the cam and the cam gear rotate about the catch arm pivot point.

In use the clamp spring of FIG. 15B provides a force on the clamping pin directed radially inward relative to the catch arm. For example, the clamp spring force may be configured to be between 10 and 22 Newtons. The position of the clamp pin is controlled in part by the cam, which either compresses the clamp spring and exposes more of the pin hole or allows the spring to relax thereby letting the pin hole to retract into the catch arm housing. In use, when the cam compresses the spring a suture needle is able to enter and exit the pin hole, but when the cam allows the spring to extend the suture needle is pinched between the pin hole and the v-notched surface of the catch arm housing. The pinching of the suture needle between these two surfaces clamps the needle in place, holding it securely during use of the device. The fixed clamp operates on the same principal and uses the same cam surface to actuate the clamp.

Figure 15C:
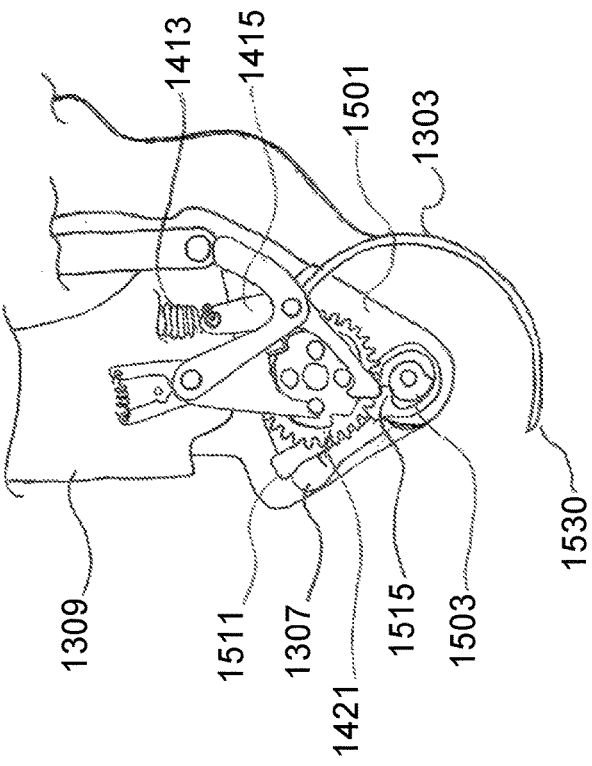
FIG. 15c is side elevation view of the distal end of the gripper mechanism in one position.

Turning now to FIG. 15C, the suturing device of FIG. 15 is depicted with the actuation lever 1309 fully depressed. The catch arm 1307 has rotated into its retracted position, and the distal tip 1530 of the suturing needle 1303 is exposed. The cam follower surface 1515 of the clamp pin 1511 has traveled along the surface of the cam 1503. The catch arm clamp pin remains in the unclamped position as the cam follower still rests on the large diameter of the cam. It is important to note that the cam has not rotated at this point. The fixed clamp 1501 also remains in the clamped position, for the same reason that the cam hasn't moved by the depression of the actuation lever. The cam rotation is coupled via the cam gear (not shown) to the windup gear 1421 and as described above, the windup gear rotates 90 degrees after a full depression and release cycle of the actuation lever. As described in the Figures above, the drive hook 1415 has indexed over and engaged the windup gear pin. Energy has been stored into the system in the form of the increased spring tension on the drive spring 1413. One important aspect of the invention that is not included in FIG. 15C is the safety shields, which at this point in the use of the device would still be protecting the user from accidentally touching the sharpened tip of the suturing needle 1303.

Figure 15D:
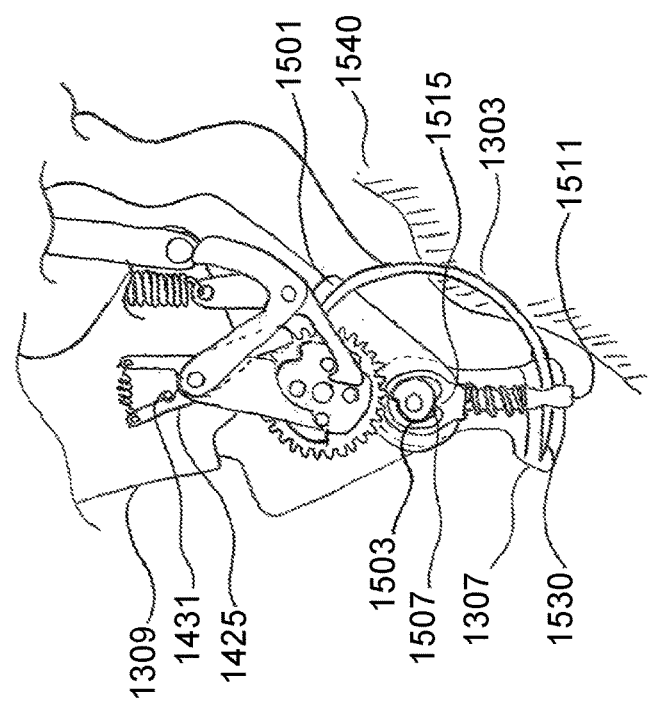
FIG. 15d is side elevation view of the gripper mechanism in another position.
Figure 15E:
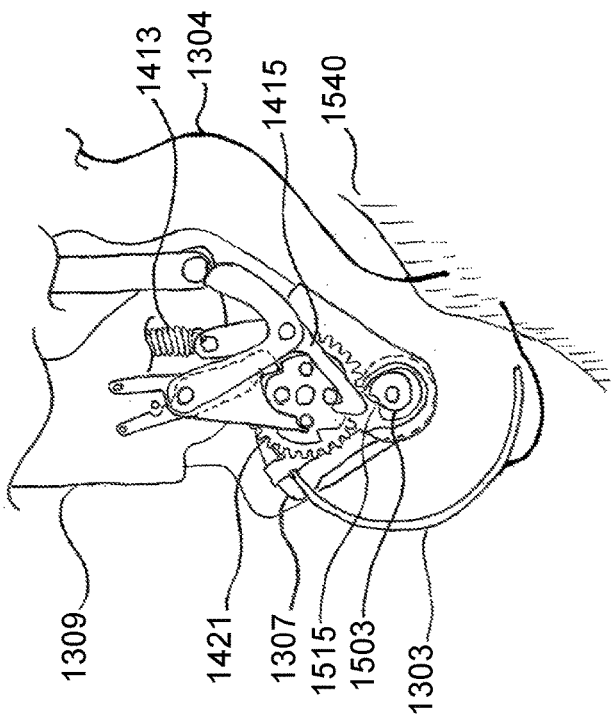
FIG. 15e is a side elevation view of the gripper mechanism in another position.
Figure 15F:
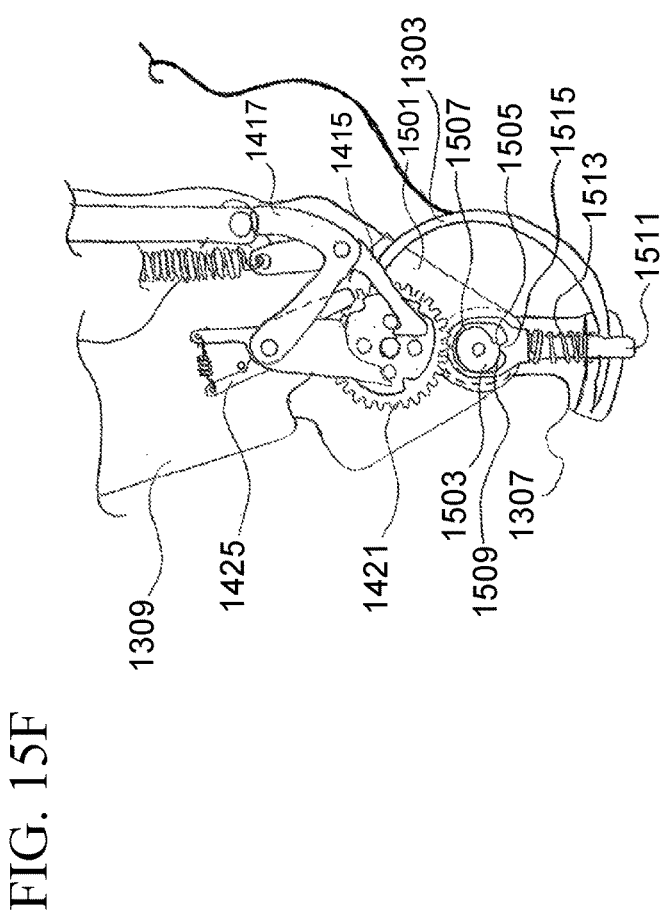
FIG. 15f is a side elevation view of the gripper mechanism in one position.

FIG. 15C represents the configuration of the clamps and the cam when the device is ready for the user to penetrate the tissue with the needle 1303, creating the needle path that will represent a completed stitch. The user would use a wrist pronating motion to deliver the needle through the tissue and once the distal end 1530 of the needle has penetrated and exited the tissue the user would release the actuation lever 1309 in order to continue using the device. FIGS. 15D-F show the internal components of the device as if the user had penetrated tissue to be sutured with the needle. For clarity, the tissue and the suture stitch will not be shown, as the internal mechanisms are the focus of the Figures. The needle will be shown being shuttled from one side of the device to the other and back and this is understood to include the penetration of the needle through the tissue and therefore the completion of the stitch.

Turning now to FIG. 15D, the suturing device is depicted with the internal mechanisms showing the configuration of the device after the penetration of the needle through the tissue 1540. The user has released the actuation lever 1309. The release of the actuation lever first returns the catch arm 1307 to its original position which covers the distal end 1530 of the needle 1303. At the very end of the actuation lever release stroke the pawl release pin 1431 on the actuation lever contacts the pawl 1425, causing the pawl to disengage from the windup gear 1421 and allowing the windup gear to rapidly rotate 90 degrees. This 90 degree rotation of the windup gear in turn causes the cam gear (not shown) to rotate 180 degrees, which in turn causes the cam 1503 to rotate 180 degrees. FIG. 15D shows the orientation of the cam after this 180 degree rotation caused by the release of the actuation lever. The smaller diameter surface of the cam 1507 has rotated under the catch arm cam follower 1515 and allowed the clamp pin 1511 to actuate radially inward. The motion of the clamp pin has captured the suture needle and pinched it between the v-notched surface of the catch arm housing and the inside of the clamp pin hole. Furthermore, the rotated position of the cam has caused the fixed clamp pin (not shown—functionally similar to the catch arm clamp pin) to actuate radially outward since the fixed clamp pin sits on the surface of the cam roughly 150 degrees from the catch arm pin. The outward radial motion of the fixed clamp pin means that the suturing needle is no longer gripped by the fixed clamp. In essence, the 180 degree rotation of the cam at the end of the actuation lever stroke has toggled the needle clamps. The fixed clamp 1501 has now released the needle and the catch arm clamp has clamped the needle.

Turning now to FIG. 15E, the user has once again depressed the actuation lever 1309. Once again the depression of the actuation lever causes the catch arm 1307 to rotate into its retracted position. Since the catch arm clamp is clamping the needle 1303 the motion of the catch arm pulls the needle through the tissue 1540, thereby completing a single suture stitch. It's worth noting again that the cam 1503 hasn't rotated during the depression of the actuation lever. The catch arm cam follower 1515 has rotated around the surface of the cam, but the follower remains on the smaller diameter of the cam, and therefore the distal end of the suturing needle remains firmly clamped by the catch arm clamp. The actuation of the lever has once again caused the drive hook 1415 to index over one pin on the windup gear 1421. The drive spring 1413 is once again under tension.

At this point in the use of the suturing device the user can remove the device from the surface of the tissue being sutured. The removal of the device pulls the suture material 1304 through the tissue. The user would pull enough material through the tissue to leave behind a satisfactory amount of suture material for tying off the stitch. The user could then cut the suture with the integrated suture cutter (not shown in FIG. 15). Once the user is satisfied with the stitch the user is able to shuttle the needle back to its starting location by releasing the actuation lever.

Turning now to FIG. 15F the user has released the actuation lever 1309 after the second lever depression stroke. Just as described above, the release of the actuation lever first causes the catch arm 1307 to return to its original position. This motion of the catch arm was described in detail above and illustrated in FIGS. 13A-D. At the very end of the release stroke the pawl release pin 1431 feature of the actuation lever contacts the pawl 1425 and causes the pawl to disengage from the windup gear 1421. This allows the windup gear to rapidly unwind, causing the windup gear to rotate 90 degrees (counter clockwise in the plane of FIG. 15F), the cam gear (not shown, described above) to rotate 180 degrees, and the cam 1503 to rotate 180 degrees. The internal components in FIG. 15F are shown after this 180 degree rotation of the cam. It should be clear that at this point the device has been returned to its starting position. The cam has rotated such that the fixed clamp is now clamping the suture needle 1303, the catch arm has released the suture needle, and the device is ready to be used to complete additional suture stitches.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is coupled to the housing and moves in a sweeping, non-linear motion relative to the housing, the actuator being operatively coupled to: (a) a first mechanism that pivots the second needle gripper between a fully extended position and a retracted position relative to the housing; and (b) a second mechanism that is operatively coupled to the first and second needle grippers and configured to alter a state of each of the first and second needle grippers to permit each respective needle gripper to either: (a) receive and grasp the suturing needle or (b) release the suturing needle.

2. The device of claim 1, wherein the first needle gripper includes a body that is fixedly attached to the handle, an elongated arm and a toggle block that is hingedly attached to the body and hingedly attached to the elongated arm, the elongated arm being operatively coupled to the second mechanism, wherein when the toggle block is in a closed position, the suturing needle is grasped thereby and when the toggle block is in an open position, the suturing needle is released and is free of the first needle gripper.

3. The device of claim 2, wherein the elongated arm is biased by a spring that is disposed between a first ledge of the body and a second ledge of the elongated arm.

4. The device of claim 1, wherein the first mechanism comprises a first set of gears that is configured such that when the actuator moves between a rest position and a fully retracted position, the second needle gripper moves between an extended at rest position and a fully retracted position relative to the housing.

5. The device of claim 4, wherein the first set of gears is located along a rear of the housing and the second mechanism includes a second set of gears that is located along a front of the housing and has a windup mechanism that is configured to store energy when the actuator is depressed and then upon release of the actuator, operating states of the first and second needle grippers are changed between a receiving position to receive the suturing needle and a locked position to capture the needle.

6. The device of claim 5, wherein the second set of gears includes a rotating cam that selectively contacts the first and second needle grippers to cause each of the first and second needle grippers to move between the receiving position and the locked, needle capturing position.

7. The device of claim 6, wherein the second set of gears includes a drive gear that is operatively connected to the rotating cam by a 2:1 gear ratio.

8. The device of claim 6, wherein the second set of gears includes a drive spring that is coupled to the actuator; a windup gear that is operatively coupled to the actuator by a linkage; and a cam gear that is coupled to the rotating cam, the second set of gears being configured such that an instroke of the actuator results in energy being stored in the drive spring and the second gripping mechanism moves from the fully extended position to the retracted position and during an outstroke of the actuator, the stored energy in the drive spring is released resulting in both the cam gear and the rotating cam rotating 180 degrees, thereby altering the state of each of the first and second needle grippers.

9. The device of claim 8, further including a biased pawl that is operatively coupled to the actuator such that during the instroke of the actuator, the pawl engages the windup gear preventing the windup gear from rotating in a first direction, wherein during a final phase of the actuator outstroke, the pawl is tripped by the actuator resulting in release of the stored energy and rotation of the windup gear a predetermined number of degrees until the pawl reengages the windup gear.

10. The device of claim 9, wherein the windup gear has four pawl engagement locations spaced 90 degrees apart from one another to allow the windup gear to rotate 90 degrees until the pawl reengages the windup gear at one of the pawl engagement locations.

11. The device of claim 6, wherein the rotating cam and the second needle gripper rotate about a common axis.

12. The device of claim 1, wherein the actuator includes an integral gear portion that is operatively coupled to a gear-ratio reducing gear that is operatively coupled to a geared surface that is associated with the second needle gripper such that rotational movement of the actuator is translated into rotational movement of the second needle gripper, wherein the actuator and integral gear portion rotate about a common axis.

13. The device of claim 1, further including a safety mechanism coupled to the housing and configured for shielding the first pointed end of the needle, the safety mechanism comprising a spring biased shield that shrouds the suturing needle during needle penetration and when the suturing needle exits the tissue, wherein the shield comprises a first shield member and a second shield member spaced from the first shield member, wherein at least one of the first and second shield members includes a tab that serves to block contact with the pointed first end of the suturing needle, the tab being positioned such that the tab lies adjacent the pointed first end of the suturing needle as it passes through the respective shield member, thereby restricting access to the pointed first end.

14. The device of claim 1, wherein a distal tip of the housing is configured to predetermine a needle trajectory through the patient's tissue, the distal tip being configured such that when the distal tip is placed on the tissue, the distal tip guides the user's rotational hand motion such that the suturing needle would initially penetrate the tissue in an acute angle orientation and is subsequently oriented into an obtuse orientation that facilitates the advancement of the suturing needle through remaining tissue.

15. The device of claim 1, further including a suture cutter disposed within the housing, the cutter including a cutter body that is pivotably coupled to the housing, the cutter body carrying a blade, and a notch to align the suture for cutting.

16. The device of claim 1, wherein the actuator is disposed along one side of the housing and protrudes outwardly therefrom, wherein the actuator pivots about an axis that is located internal to the housing and lies at a location between the distal and proximal ends of the housing.

17. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is coupled to the housing and is also coupled to: (a) a first mechanism that pivots the second needle gripper between a fully extended position and a retracted position relative to the housing; and (b) a second mechanism that is operatively coupled to the first and second needle grippers and configured to alter a state of each of the first and second needle grippers to permit each respective needle gripper to either: (a) receive and grasp the suturing needle or (b) release the suturing needle;
wherein in the retracted position, the second needle gripper is at least partially disposed within the housing and the first needle gripper remains stationary within the housing;
wherein in a first operating position, the suturing needle is grasped entirely by the first needle gripper and is free of contact with the second needle gripper and in a second operating position, the suturing needle is grasped entirely by the second needle gripper and is free of contact with the first needle gripper.

18. The device of claim 17, wherein the actuator is configured such that: (1) during a first instroke of the actuator, the second needle gripper rotates to the retracted position away from and exposes the suturing needle which is being held by the first needle gripper; (2) during a first outstroke of the actuator, the second needle gripper rotates to the fully extended position onto the suturing needle and the second mechanism causes the suturing needle to be grasped by the second needle gripper; (3) during a second instroke of the actuator, the suturing needle is held by the second needle gripper and the second needle gripper is rotated to the retracted position; and (4) during a second outstroke of the actuator, the second needle gripper is rotated to the fully extended position and the needle is transferred to the first needle gripper as a result of the second mechanism altering the states of the first and second needle grippers.

19. The device of claim 17, wherein the actuator moves in a sweeping, non-linear motion relative to the housing and is located along one side of the housing and during an instroke of the actuator, the actuator is substantially contained within a hollow interior of the housing.

20. A device for suturing tissue comprising:
a handle including a housing having a distal end and an opposite proximal end;
a suturing needle for advancing a suture through the tissue, the suturing needle having a first pointed end and an opposite second end;
a first needle gripper coupled to the housing, the first needle gripper being configured to both grasp and release the suturing needle;
a second needle gripper coupled to the housing, the second needle gripper being configured to both grasp and release the suturing needle; and
an actuator that is coupled to the housing and moves in a sweeping, non-linear motion relative to the housing, the actuator being operatively coupled to: (a) a first mechanism that rotates the second needle gripper between a fully extended position and a retracted position relative to the housing, wherein the second needle gripper rotates in a first direction to reach the fully extended position and rotates in an opposite second direction to reach the retracted position; and (b) a second mechanism that is operatively coupled to the first and second needle grippers and configured to alter a state of each of the first and second needle grippers to permit each respective needle gripper to either: (a) receive and grasp the suturing needle or (b) release the suturing needle.

21. The device of claim 20, wherein in a first operating position, the suturing needle is grasped entirely by the first needle gripper and is free of contact with the second needle gripper and in a second operating position, the suturing needle is grasped entirely by the second needle gripper and is free of contact with the first needle gripper.

* * * * *